(12) United States Patent
Elias et al.

(10) Patent No.: US 12,320,914 B2
(45) Date of Patent: Jun. 3, 2025

(54) METHODS FOR DETECTING OCCUPANCY AND DETERMINING VALUE CHAIN RECOMMENDATIONS USING RADIO SIGNALS

(71) Applicant: STRONG FORCE VCN PORTFOLIO 2019, LLC, Fort Lauderdale, FL (US)

(72) Inventors: Stephen Paul Elias, Nashua, NH (US); Eric Roger Giler, Boston, MA (US); Katherine Lavin Hall, Arlington, MA (US); Charles Howard Cella, Pembroke, MA (US)

(73) Assignee: STRONG FORCE VCN PORTFOLIO 2019, LLC, Fort Lauderdale, FL (US)

( * ) Notice: Subject to any disclaimer, the term of this patent is extended or adjusted under 35 U.S.C. 154(b) by 207 days.

(21) Appl. No.: 17/332,500

(22) Filed: May 27, 2021

(65) Prior Publication Data
US 2021/0356576 A1    Nov. 18, 2021

Related U.S. Application Data

(63) Continuation of application No. PCT/US2020/041151, filed on Jul. 8, 2020.
(Continued)

(51) Int. Cl.
*G01S 7/00* (2006.01)
*F24F 11/49* (2018.01)
(Continued)

(52) U.S. Cl.
CPC .............. *G01S 7/006* (2013.01); *F24F 11/49* (2018.01); *G01S 13/003* (2013.01); *G01S 13/56* (2013.01);
(Continued)

(58) Field of Classification Search
None
See application file for complete search history.

(56) References Cited

U.S. PATENT DOCUMENTS

| | | |
|---|---|---|
| 5,475,868 A | 12/1995 | Duque-Anton et al. |
| 2009/0295534 A1 | 12/2009 | Golander et al. |
| | (Continued) | |

FOREIGN PATENT DOCUMENTS

| | | |
|---|---|---|
| CN | 107003397 A | 8/2017 |
| CN | 108738356 A | 11/2018 |
| | (Continued) | |

OTHER PUBLICATIONS

Banerjee, A. et al., "Through Wall People Localization Exploiting Radio Windows," Jul. 27, 2013, https://arxiv.org/pdf/1307.7233v1.pdf, 14 pages.
(Continued)

*Primary Examiner* — Whitney Moore
(74) *Attorney, Agent, or Firm* — RMCK Law Group, PLC

(57) ABSTRACT

A sensor system for determining occupancy in a space generally includes a transmitter radio device that transmits radio signals over a channel in the space; a receiver radio device that receives the transmitted radio signals that have traveled through the space; and at least one processor implementing an occupancy-centric algorithm that determines occupancy in the space based on the radio signals. The at least one processor determines channel state information based on the radio signals transmitted over the channel, determines occupancy in the space based on the channel state information, and outputs an occupancy signal based on the determined occupancy.

20 Claims, 4 Drawing Sheets

Related U.S. Application Data

(60) Provisional application No. 62/871,235, filed on Jul. 8, 2019.

(51) Int. Cl.

| | | |
|---|---|---|
| *F24F 120/12* | (2018.01) | |
| *F24F 120/14* | (2018.01) | |
| *G01S 13/00* | (2006.01) | |
| *G01S 13/56* | (2006.01) | |
| *G05B 15/02* | (2006.01) | |
| *G06F 18/214* | (2023.01) | |
| *G06N 5/04* | (2023.01) | |
| *G06N 20/00* | (2019.01) | |
| *G06Q 10/0631* | (2023.01) | |
| *G06Q 10/0639* | (2023.01) | |
| *G06Q 10/08* | (2024.01) | |
| *G16H 40/67* | (2018.01) | |
| *G16H 50/20* | (2018.01) | |
| *G16H 50/30* | (2018.01) | |
| *G16H 50/70* | (2018.01) | |

(52) U.S. Cl.
 CPC ........... *G05B 15/02* (2013.01); *G06F 18/214* (2023.01); *G06N 5/04* (2013.01); *G06N 20/00* (2019.01); *G06Q 10/06312* (2013.01); *G06Q 10/06315* (2013.01); *G06Q 10/06398* (2013.01); *G06Q 10/08* (2013.01); *G16H 40/67* (2018.01); *G16H 50/20* (2018.01); *G16H 50/30* (2018.01); *G16H 50/70* (2018.01); *F24F 2120/12* (2018.01); *F24F 2120/14* (2018.01)

(56) References Cited

U.S. PATENT DOCUMENTS

| | | | |
|---|---|---|---|
| 2011/0148689 A1 | 6/2011 | Filippi et al. | |
| 2012/0066168 A1 | 3/2012 | Fadell et al. | |
| 2012/0262327 A1 | 10/2012 | Hester et al. | |
| 2016/0019497 A1* | 1/2016 | Carvajal | H04L 67/104 705/333 |
| 2017/0086202 A1 | 3/2017 | Chen | |
| 2017/0309146 A1 | 10/2017 | MacKenzie et al. | |
| 2017/0323274 A1* | 11/2017 | Johnson | G05B 13/041 |
| 2017/0343658 A1* | 11/2017 | Ramirez | G01S 13/56 |
| 2018/0292520 A1 | 10/2018 | Bermudez et al. | |
| 2019/0188797 A1* | 6/2019 | Przechocki | H04L 67/125 |
| 2019/0327124 A1* | 10/2019 | Lai | G01S 5/017 |
| 2020/0245423 A1 | 7/2020 | Honjo et al. | |
| 2020/0320454 A1 | 10/2020 | Almashor et al. | |
| 2021/0279549 A1 | 9/2021 | Spanos et al. | |
| 2021/0356575 A1 | 11/2021 | Elias et al. | |
| 2021/0374886 A1 | 12/2021 | Reitz et al. | |

FOREIGN PATENT DOCUMENTS

| | | |
|---|---|---|
| DE | 102014211237 A1 | 12/2015 |
| DE | 102014217504 A1 | 3/2016 |
| KR | 101615865 B1 | 4/2016 |
| KR | 20170083365 A | 7/2017 |
| WO | 2018191730 A1 | 10/2018 |

OTHER PUBLICATIONS

Extended European Search Report dated Jun. 16, 2023 for EP Application No. 20836707.8, 7 pages.

PCT International Search Report and Written Opinion mailed Oct. 29, 2020 for International Application No. PCT/US2020/041151, 10 pages.

\* cited by examiner

METHODS FOR DETECTING OCCUPANCY AND DETERMINING VALUE CHAIN RECOMMENDATIONS USING RADIO SIGNALS

CROSS-REFERENCE TO RELATED APPLICATIONS

This application is a bypass continuation of International Application No. PCT/US2020/041151, filed Jul. 8, 2020, which claims the benefit of U.S. Provisional Application No. 62/871,235, filed on Jul. 8, 2019. The disclosure of each of the above applications are incorporated herein by reference in their entirety.

FIELD

This disclosure relates to sensing and monitoring, and more specifically to sensing and monitoring certain spaces and areas for human occupancy. This disclosure is also related to sensing and monitoring movement or changes in an environment, including movement by animals and objects. This disclosure is also related to using sensor and/or monitor information to control certain systems within commercial and residential facilities, including, but not limited to; heating, cooling, ventilation, security, lighting, power, and entertainment systems and the like. This disclosure also may be used to determine human occupancy in outdoor spaces and to control certain outdoor systems including, but not limited to; heating, cooling, ventilation, security, lighting, power, and entertainment systems and the like.

BACKGROUND

Heating, ventilating and cooling (HVAC) systems in buildings account for a large percentage of overall energy usage. It is estimated that in the United States, approximately 13% of all current energy usage is for HVAC systems in buildings. Because the energy usage for these systems is so high, there is an opportunity to save substantial amounts of energy if these systems can be made more efficient. One source of inefficiency is that HVAC systems are often running at maximum capacity or at capacities optimized for fully occupied buildings even when buildings or spaces within buildings are unoccupied or under-occupied (not fully occupied). Therefore, energy could be saved if sensors and/or monitors existed that could detect if a building or space was occupied or under-occupied and adjust the HVAC system to the appropriate level for the unoccupied or under-occupied conditions. For example, less heating and cooling could be supplied to a building when it is unoccupied. Adjusting temperature levels to lower levels when the outdoor temperature is low and to higher temperatures when the outdoor temperature is high is sometimes referred to as enabling temperature setbacks.

A variety of sensor types have been developed to detect occupancy in buildings or in portions of buildings, including carbon dioxide ($CO_2$) sensors, passive infrared (PIR) sensors, motion sensors, ultrasonic and/or sound sensors, image/video sensors, and electronic device sensors. While there are advantages associated with these various types of sensors, as stand-alone solutions they are non-optimal because of some combination of inaccurate performance, high deployment and/or maintenance costs, requirements for phones/tags/beacons that must be worn or carried by an occupant, complicated user interfaces, and privacy concerns. Therefore, a need has been identified for a new type of sensor system that is low-cost, low-maintenance, easy to install and set-up, does not require occupants to have phones, beacons or RF tags/IDs, and does not collect any personally identifiable information.

SUMMARY

In embodiments, a sensor system for determining occupancy in a space includes a transmitter radio device that transmits radio signals over a channel in the space; a receiver radio device that receives the transmitted radio signals that have traveled through the space; and at least one processor implementing an occupancy-centric algorithm that determines occupancy in the space based on the radio signals. In embodiments, the at least one processor: determines channel state information based on the radio signals transmitted over the channel, determines occupancy in the space based on the channel state information, and outputs an occupancy signal based on the determined occupancy.

In embodiments, the at least one processor is integrated with the receiver radio device.

In embodiments, the at least one processor is integrated with the transmitter radio device.

In embodiments, the system includes a computing device and the at least one processor is integrated with the computing device. In embodiments, the at least one processor outputs a control signal to a control system. In embodiments, the control system is associated with a heating, ventilating, and cooling system for the space.

In embodiments, the control system is associated with a security system for the space. In embodiments, the control system is associated with a lighting system for the space. In embodiments, the control system is associated with a power system for the space. In embodiments, the control system is associated with an entertainment system for the space.

In embodiments, the radio signals comprise one or more subcarriers, and the at least one processor: (i) analyzes amplitude information associated with the one or more subcarriers, and (ii) determines the occupancy in the space based on the amplitude information. In embodiments, the radio signals comprise one or more subcarriers, and the at least one processor: (i) analyzes standard deviations of amplitude and phase signals associated with the one or more subcarriers, and (ii) determines occupancy in the space based on the standard deviations of amplitude and phase signals. In embodiments, the radio signals comprise one or more subcarriers, and the at least one processor: (i) analyzes temporal and frequency correlations of amplitude and phase signals associated with the one or more subcarriers, and (ii) determines occupancy in the space based on the temporal and frequency correlations of amplitude and phase signals. In embodiments, the radio signals comprise one or more subcarriers, and the at least one processor: (i) analyzes averages of amplitude and phase signals associated with the one or more subcarriers, and (ii) determines occupancy in the space based on the averages of amplitude and phase signals. In embodiments, the radio signals comprise one or more subcarriers, and the at least one processor: (i) analyzes energy in the peaks of CSI amplitude and phase signals associated with the one or more subcarriers, and (ii) determines occupancy in the space based on the energy in the peaks of CSI amplitude and phase signals.

In embodiments, the occupancy-centric algorithm is configured to determine occupancy in the space based on changes in one or more of signal amplitude, energy, amplitude change, energy change, amplitude spread, energy spread, amplitude spread change, and energy spread change of the radio signals.

In embodiments, a method for determining occupancy in a space includes transmitting radio signals over a channel in the space; receiving the transmitted radio signals that have traveled through the space; and implementing an occupancy-centric algorithm with at least one processor that determines occupancy in the space based on the radio signals, that determines channel state information based on the radio signals transmitted over the channel, that determines occupancy in the space based on the channel state information, and that outputs an occupancy signal based on the determined occupancy.

In embodiments, the at least one processor is integrated with the receiver radio device that receives the transmitted radio signals that have traveled through the space. In embodiments, the at least one processor is integrated with the transmitter radio device that transmitted radio signals over the channel in the space.

In embodiments, the method includes outputting a control signal to a control system with the at least one processor, and the control system is associated with a heating, ventilating, and cooling system for the space. In embodiments, the method includes outputting a control signal to a control system with the at least one processor, and the control system is associated with a security system for the space. In embodiments, the method includes outputting a control signal to a control system with the at least one processor, and the control system is associated with a lighting system for the space. In embodiments, the method includes outputting a control signal to a control system with the at least one processor, and the control system is associated with a power system for the space. In embodiments, the method includes outputting a control signal to a control system with the at least one processor, and the control system is associated with an entertainment system for the space.

In embodiments, the radio signals comprise one or more subcarriers, and the at least one processor: (i) analyzes amplitude information associated with the one or more subcarriers, and (ii) determines the occupancy in the space based on the amplitude information. In embodiments, the radio signals comprise one or more subcarriers, and the at least one processor: (i) analyzes standard deviations of amplitude and phase signals associated with the one or more subcarriers, and (ii) determines occupancy in the space based on the standard deviations of amplitude and phase signals. In embodiments, the radio signals comprise one or more subcarriers, and the at least one processor: (i) analyzes temporal and frequency correlations of amplitude and phase signals associated with the one or more subcarriers, and (ii) determines occupancy in the space based on the temporal and frequency correlations of amplitude and phase signals. In embodiments, the radio signals comprise one or more subcarriers, and the at least one processor: (i) analyzes averages of amplitude and phase signals associated with the one or more subcarriers, and (ii) determines occupancy in the space based on the averages of amplitude and phase signals. In embodiments, the radio signals comprise one or more subcarriers, and the at least one processor: (i) analyzes energy in the peaks of CSI amplitude and phase signals associated with the one or more subcarriers, and (ii) determines occupancy in the space based on the energy in the peaks of CSI amplitude and phase signals. In embodiments, the occupancy-centric algorithm is configured to determine occupancy in the space based on changes in one or more of signal amplitude, energy, amplitude change, energy change, amplitude spread, energy spread, amplitude spread change, and energy spread change of the radio signals.

In embodiments, a sensor system for determining occupancy in a space includes a transmitter radio device that transmits radio signals over a channel in the space; a receiver radio device that receives the transmitted radio signals that have traveled through the space; and at least one processor implementing an occupancy-centric algorithm that determines occupancy in the space based on the radio signals, the at least one processor: determines channel state information based on the radio signals transmitted over the channel, determines occupancy in the space based on the channel state information, determines a value chain recommendation based on the occupancy in the space of a value chain network, and outputs an occupancy signal based on the determined occupancy and the value chain recommendation.

In embodiments, the value chain recommendation relates to a health of one or more workers. In embodiments, the value chain recommendation relates to allocation or reallocation of worker resources based on the occupancy in the space. In embodiments, the value chain recommendation is based on productivity of workers in the space.

In embodiments, the value chain recommendation is associated with at least one of an activation or deactivation of at least one of a heating system, a ventilating system, a cooling system, a security system, a lighting system, a kitchen system, a speaker system, a power system, and an entertainment system for the space.

In embodiments, the occupancy-centric algorithm evolves such that the value chain recommendation is redetermined based on the evolution of the occupancy-centric algorithm. In embodiments, the value chain recommendation is determined based on a machine learning system that trains machine-learned models that output logistics design recommendations based on training data sets that each respectively defines one or more features of a respective logistic system and an outcome relating to the respective logistics system. In embodiments, the value chain recommendation is determined based on an artificial intelligence system that receives a request for a logistics system design recommendation and determines the logistics system design recommendation based on one or more machine-learned models and the request. In embodiments, the value chain recommendation is determined by a digital twin system that generates an environment digital twin of a logistics environment that incorporates a logistics system design recommendation, and one or more physical asset digital twins of physical assets, the digital twin system executes a simulation based on the logistics environment digital twin, the one or more physical asset digital twins. In embodiments, the value chain recommendation is based on logistics factors that include one or more of: a type of product corresponding to the proposed logistics solution, one or more features of the type of product, a location of a manufacturing site, a location of a distribution facility, a location of a warehouse, a location of a customer base, proposed expansion areas of the organization, and supply chain features. In embodiments, the value chain recommendation is based on logistics value chain network entities that are selected from the group consisting of products, suppliers, producers, manufacturers, retailers, businesses, owners, operators, operating facilities, customers, consumers, workers, mobile devices, wearable devices, distributors, resellers, supply chain infrastructure facilities, supply chain processes, logistics processes, reverse logistics processes, demand prediction processes, demand management processes, demand aggregation processes, machines, ships, barges, warehouses, maritime ports, airports, airways, waterways, roadways, railways, bridges, tunnels, online retailers, e-commerce sites, demand factors, supply factors, delivery systems, floating assets, points of origin, points of destination, points of storage, points of use, networks, information technology systems, software platforms, distribution centers, fulfillment centers, containers, container handling facilities, customs, export control, border control, drones, robots, autonomous vehicles, hauling facilities, drones/robots/AVs, waterways, and port infrastructure facilities.

In embodiments, the supply chain infrastructure facilities are facilities selected from the group consisting of a ship, container ship, boat, barge, maritime port, crane, container, container handling, shipyard, maritime dock, warehouse, distribution, fulfillment, fueling, refueling, nuclear refueling, waste removal, food supply, beverage supply, drone, robot, autonomous vehicle, aircraft, automotive, truck, train, lift, forklift, hauling facilities, conveyor, loading dock, waterway, bridge, tunnel, airport, depot, vehicle station, train station, weigh station, inspection, roadway, railway, highway, customs house, and border control facilities.

In embodiments, the value chain recommendation is based on supply factors that are selected from the group consisting of component availability, material availability, component location, material location, component pricing, material pricing, taxation, tariff, impost, duty, import regulation, export regulation, border control, trade regulation, customs, navigation, traffic, congestion, vehicle capacity, ship capacity, container capacity, package capacity, vehicle availability, ship availability, container availability, package availability, vehicle location, ship location, container location, port location, port availability, port capacity, storage availability, storage capacity, warehouse availability, warehouse capacity, fulfillment center location, fulfillment center availability, fulfillment center capacity, asset owner identity, system compatibility, worker availability, worker competency, worker location, goods pricing, fuel pricing, energy pricing, route availability, route distance, route cost, and route safety factors.

In embodiments, the value chain recommendation is determined based on a machine learning/artificial intelligence system determining a problem state based on a detected stress level of humans along a supply chain. In embodiments, the value chain recommendation is determined based on disruptions in the space of the value chain network. In embodiments, the value chain recommendation includes operating recommendations needed to compensate for changes in operating parameters. In embodiments, the value chain recommendation is determined from physical activities data and worker data in order to improve value chain workflows. In embodiments, the value chain recommendation includes suggestions for removing or limiting worker redundancies for a workflow.

In embodiments, a method for determining occupancy in a space includes transmitting radio signals over a channel in the space; receiving the transmitted radio signals that have traveled through the space; and implementing with at least one processor an occupancy-centric algorithm that determines occupancy in the space based on the radio signals, that determines channel state information based on the radio signals transmitted over the channel, that determines occupancy in the space based on the channel state information, that determines a value chain recommendation based on the occupancy in the space of a value chain network, and that outputs an occupancy signal based on the determined occupancy and the value chain recommendation.

In embodiments, the value chain recommendation relates to a health of one or more workers. In embodiments, the value chain recommendation relates to allocation or reallocation of worker resources based on the occupancy in the space. In embodiments, the value chain recommendation is based on productivity of workers in the space. In embodiments, the value chain recommendation is associated with at least one of an activation or deactivation of at least one of a heating system, a ventilating system, a cooling system, a security system, a lighting system, a kitchen system, a speaker system, a power system, and an entertainment system for the space.

In embodiments, the occupancy-centric algorithm evolves such that the value chain recommendation is redetermined based on the evolution of the occupancy-centric algorithm. In embodiments, the value chain recommendation is determined based on a machine learning system that trains machine-learned models that output logistics design recommendations based on training data sets that each respectively defines one or more features of a respective logistic system and an outcome relating to the respective logistics system. In embodiments, the value chain recommendation is determined based on an artificial intelligence system that receives a request for a logistics system design recommendation and determines the logistics system design recommendation based on one or more machine-learned models and the request.

In embodiments, the value chain recommendation is determined by a digital twin system that generates an environment digital twin of a logistics environment that incorporates a logistics system design recommendation, and one or more physical asset digital twins of physical assets, the digital twin system executes a simulation based on the logistics environment digital twin, the one or more physical asset digital twins.

In embodiments, the value chain recommendation is based on logistics factors that include one or more of: a type of product corresponding to the proposed logistics solution, one or more features of the type of product, a location of a manufacturing site, a location of a distribution facility, a location of a warehouse, a location of a customer base, proposed expansion areas of the organization, and supply chain features.

In embodiments, the value chain recommendation is based on logistics value chain network entities that are selected from the group consisting of products, suppliers, producers, manufacturers, retailers, businesses, owners, operators, operating facilities, customers, consumers, workers, mobile devices, wearable devices, distributors, resellers, supply chain infrastructure facilities, supply chain processes, logistics processes, reverse logistics processes, demand prediction processes, demand management processes, demand aggregation processes, machines, ships, barges, warehouses, maritime ports, airports, airways, waterways, roadways, railways, bridges, tunnels, online retailers, e-commerce sites, demand factors, supply factors, delivery systems, floating assets, points of origin, points of destination, points of storage, points of use, networks, information technology systems, software platforms, distribution centers, fulfillment centers, containers, container handling facilities, customs, export control, border control, drones, robots, autonomous vehicles, hauling facilities, drones/robots/AVs, waterways, and port infrastructure facilities.

In embodiments, the supply chain infrastructure facilities are facilities selected from the group consisting of a ship, container ship, boat, barge, maritime port, crane, container, container handling, shipyard, maritime dock, warehouse, distribution, fulfillment, fueling, refueling, nuclear refueling, waste removal, food supply, beverage supply, drone, robot, autonomous vehicle, aircraft, automotive, truck, train, lift, forklift, hauling facilities, conveyor, loading dock, waterway, bridge, tunnel, airport, depot, vehicle station, train station, weigh station, inspection, roadway, railway, highway, customs house, and border control facilities.

In embodiments, the value chain recommendation is based on supply factors that are selected from the group consisting of component availability, material availability, component location, material location, component pricing, material pricing, taxation, tariff, impost, duty, import regulation, export regulation, border control, trade regulation, customs, navigation, traffic, congestion, vehicle capacity, ship capacity, container capacity, package capacity, vehicle availability, ship availability, container availability, package availability, vehicle location, ship location, container location, port location, port availability, port capacity, storage availability, storage capacity, warehouse availability, warehouse capacity, fulfillment center location, fulfillment center availability, fulfillment center capacity, asset owner identity, system compatibility, worker availability, worker competency, worker location, goods pricing, fuel pricing, energy pricing, route availability, route distance, route cost, and route safety factors.

In embodiments, the value chain recommendation is determined based on a machine learning/artificial intelligence system determining a problem state based on a detected stress level of humans along a supply chain. In embodiments, the value chain recommendation is determined based on disruptions in the space of the value chain network. In embodiments, the value chain recommendation includes operating recommendations needed to compensate for changes in operating parameters. In embodiments, the value chain recommendation is determined from physical activities data and worker data in order to improve value chain workflows.

In embodiments, the value chain recommendation includes suggestions for removing or limiting worker redundancies for a workflow.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

DETAILED DESCRIPTION

Figure 1A:
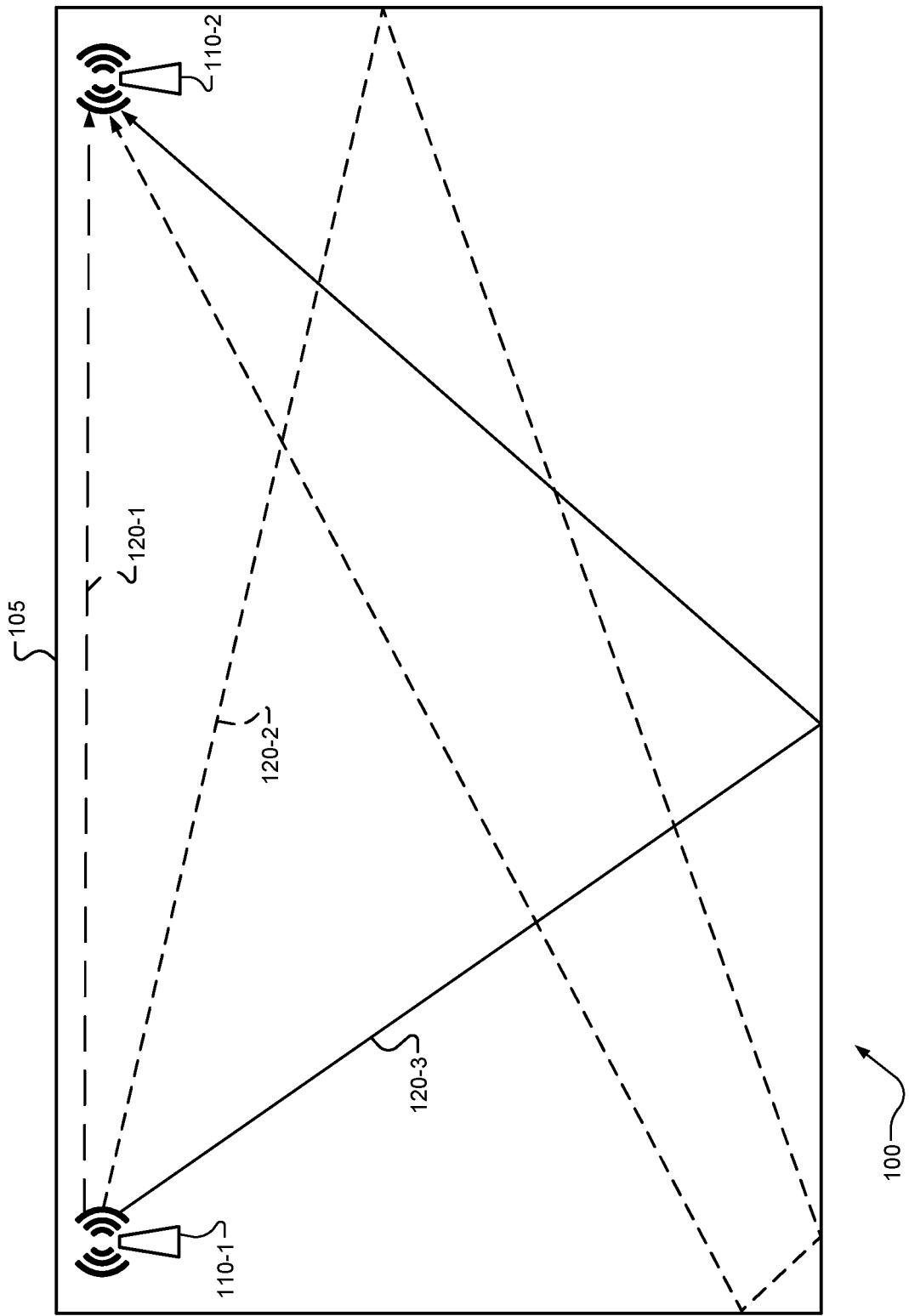
FIGS. 1A and 1B are schematic diagrams illustrating an example sensor system according to various implementations arranged within a space that is empty of a human and includes a human, respectively.

This disclosure is related to a new type of occupancy sensor that analyzes radio signals to determine occupancy in a space or a building. In this disclosure, the terms space, area, vicinity, and/or region may refer to spaces, areas, vicinities, regions and the like either inside or outside rooms, apartments, condos, homes, buildings, structures, shelters, and similar geographic locations. The occupancy sensor of the present disclosure can be used as a stand-alone sensor and/or along-side, and may integrate signals from, previously developed or yet-to-be-developed sensors and sensor systems. In this disclosure, we may refer to such sensors and sensor systems as other sensors and/or other sensor systems.

The techniques of the present disclosure utilize electronic devices that may send and receive radio signals. These devices may be referred to as radio devices, wireless devices, access points, routers, hubs, hotspots, radios, transceivers, antennas, and the like. These devices may be integrated into other electronic devices, such as access points, routers, modems, phones, computers, tablets, watches, speakers, thermostats, appliances, lighting devices, e-readers, furniture, vehicles, cameras, GPS devices, drones, and/or personal assistants (e.g., Google Home™, Amazon Echo™, Apple HomePod™). These devices may communicate with other devices using standardized signaling protocols such as WiFi, Bluetooth™, ZigBee™, 5G, ultrawideband (UWB), any of the IEEE standards including but not limited to IEEE 802.11, IEEE 802.15.1, IEEE 802.15.3 IEEE 802.15.4, IEEE 802.16, IEEE IMT-Advanced/3GPP, Long Term Evolution (LTE), and NFC (near field communication). Additionally or alternatively, these devices may communicate using customized and/or proprietary signaling protocols. It should be understood that this disclosure may include any type of radio, radio card, and/or radio device that can send and receive signals in the radio frequency or RF region of the electromagnetic spectrum. It should also be understood that this disclosure may include any device that comprises, includes, is embedded in, and/or is attached to radio devices.

The radio devices of this disclosure may include one or more antennas for transmitting signals, one or more antennas for receiving signals and/or one or more antennas for both transmitting and receiving signals. In some embodiments, antennas may be switched in and out of circuits in the radio device, and/or any other electronic circuits attached to said radio device, either electronically or manually. Radio devices may have one or more antennas. Antennas may be omni-directional, nearly omni-directional, multi-directional, or uni- or nearly uni-directional. Multiple antennas may be driven in coordination to direct a radio signal in a desired direction. The direction of radio signal propagation may be changed and/or tuned. In embodiments, radio signals sent by a single device but transmitted by different antennas may experience different radio environments.

The radio frequency range of the signals transmitted and received by these antennas may be single frequency or multiple frequency, narrowband or broadband, single channel or multichannel, static or adjustable. The radio signals may comprise subcarriers and/or subcarrier groups and/or sub channels. The radio signals may be frequency multiplexed. The radio signals used in this disclosure may be frequency hopped, and they may be able to carry multiple signals on different RF channels (carrier frequencies).

The signals generated and received via the antennas may be amplitude modulated, frequency modulated, phase modulated, pulse-width modulated, polarization modulated and/or may be generated using any combination of modulation schemes. In embodiments, any suitable modulation format can be used, including, but not limited to, analog modulation, digital modulation, amplitude modulation and variants thereof (AM), frequency modulation and variants thereof (FM), phase modulation (PM) and variants thereof, polarization modulation and variants thereof, double-sideband modulation (DSB) and variants thereof, single-sideband modulation (SSB) and variants thereof, quadrature amplitude modulation (QAM) and variants thereof, orthogonal frequency division multiplexing (OFDM) and variants thereof, spread spectrum and variants thereof, and code-division multiplexing and variants thereof.

Figure 1B:
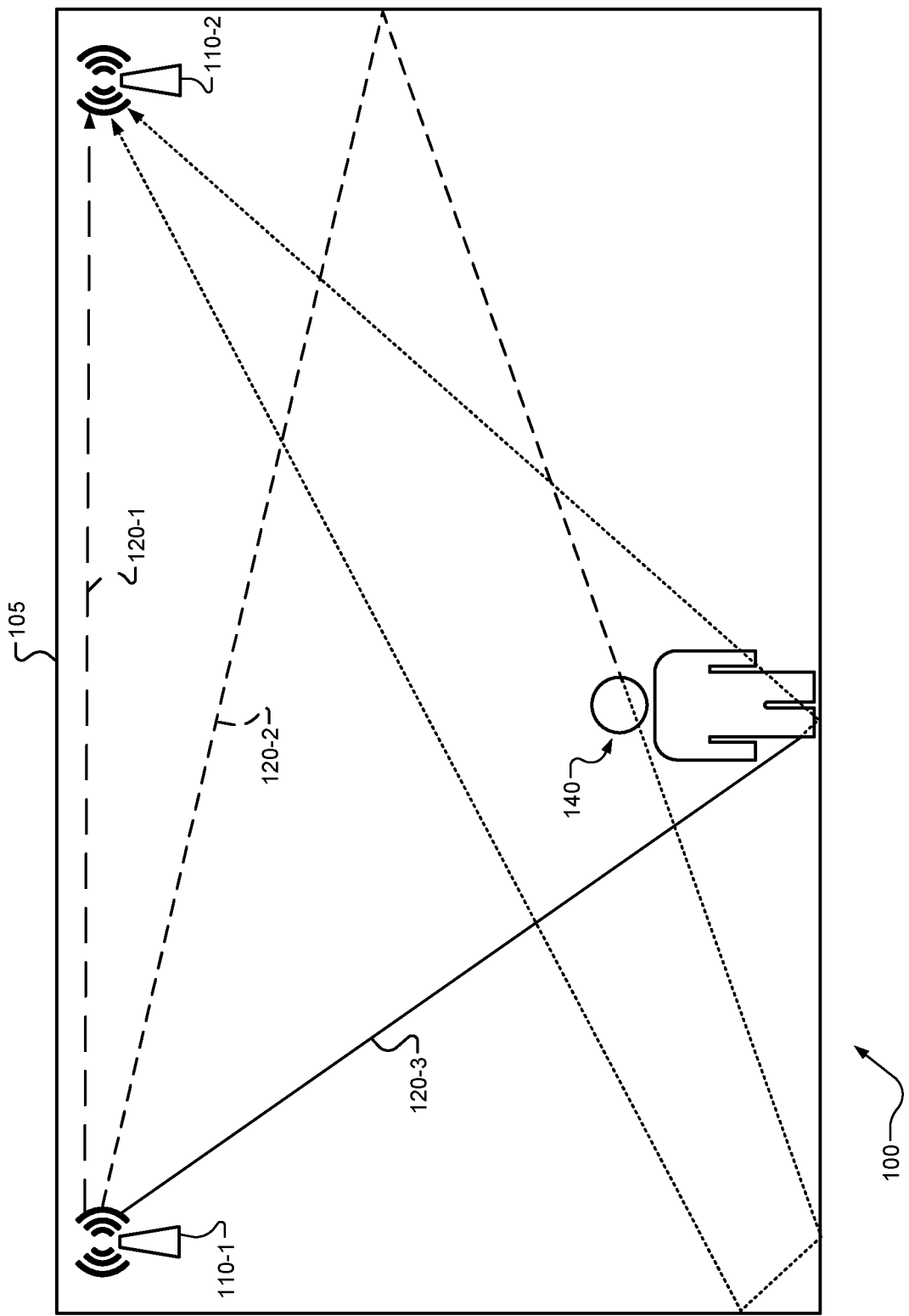

With reference to FIGS. 1A and 1B, an example sensor system 100 according to some implementations of the present disclosure can comprise at least two radio devices 110 that may send and/or receive signals arranged within a space 105. A transmitter radio device 110-1 may transmit a radio signal to a receiver radio device 110-2. The receiver radio device 110-2 may receive and process the transmitted radio signal. Although the radio devices 110 are described as "transmitter" radio device 110-1 and "receiver" radio device 110-2, it should be appreciated that the transmitter radio device 110-1 may also have the capability to receive radio signals, and the receiver radio device 110-2 may also have the capability to transmit radio signals. For ease of description, the present disclosure will describe transmission of the radio signals from the transmitter radio device 110-1 to be received at the receiver radio device 110-2, but it should be understood that, in some implementations, each radio device 110 can both transmit and receive radio signals. In embodiments, there are no requirements that radio devices 110 be the same types of devices. For example, radio device 110-1 may be a computer and radio device 110-2 may be an access point. Each radio device 110 may be any of the radio devices described in this disclosure. In some embodiments, the at least two radio devices 110 may be similar devices, or may be replicas of each other.

Figure 2:
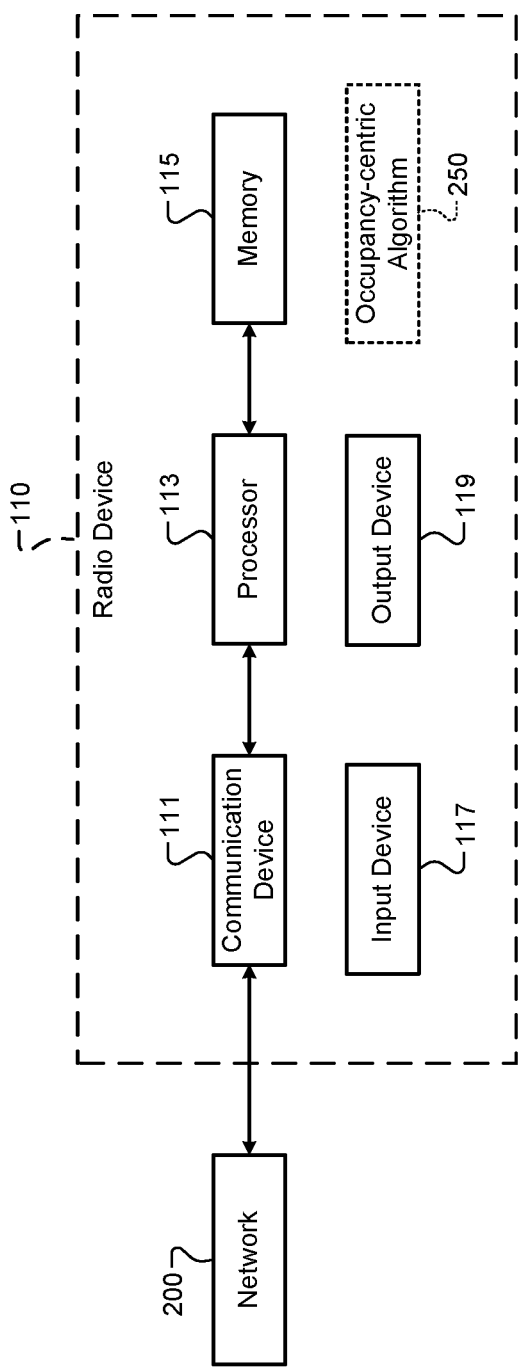
FIG. 2 is a functional block diagram of a radio device included in the example sensor system of FIG. 1.

With additional reference to FIG. 2, a functional block diagram of an example radio device 110 is illustrated. The radio device 110 can represent the configurations of the transmitter and receiver radio devices 110-1, 110-2. It will be appreciated that the one or both of the transmitter and receiver radio devices 110-1, 110-2 may differ from the illustrated radio device 110. The radio device 110 can include a communication device 111 (e.g., a wireless transceiver) configured for communication with other radio devices 110 or other communication devices, e.g., via a network 200 or otherwise. A processor 113 can be configured to control operation of the radio device 110. The term "processor" as used herein can refer to both a single processor and two or more processors operating in a parallel or distributed architecture.

A memory 115 can be included and take the form of any suitable storage medium (flash, hard disk, etc.) configured to store information at the radio device 110. In one implementation, the memory 115 can store instructions executable by the processor 113 to cause the radio device 110 to perform at least a portion of the disclosed techniques. Any or all the processing and memory functions of the radio device may be performed remotely on a nearby piece of hardware, or remotely on captive hardware or on shared hardware components and various cloud network facilities. The radio device 110 can also include an input device 117 and an output device 119. The input device 117 can be any hardware device configured to accept input to the radio device 110. In some examples, the input device 117 may receive at least one input signal from a button or dial or knob or display that is manipulated by a user or occupant indicating that a human is present in the space 105 or is leaving the space 105 or other information that may be input to the system. By way of these examples, the input device 117 may receive at least one or more signals from a communication device with information from a user or occupant that indicates whether the space 105 is currently or was recently occupied, or indicating periods of time when the space 105 was occupied or unoccupied. Similarly, the output device 119 can be any hardware device configured to provide an output from the radio device 110. In embodiments, the output device 119 may light up, make a noise, send a communication signal to at least one other electronic device, or the like. The output device may include a display and user interface that may be configured to prompt an input signal from a user or occupant of the space 105. While not shown, it will be appreciated that the radio device 110 can include other suitable components, such as a display (a touch display), physical buttons, a camera, and the like. As further described below, the example sensor system 100 can be configured to perform various techniques for sensing occupancy in a space 105 utilizing radio signals.

Different portions of the transmitted signal may follow different spatial paths, such as first path 120-1, second path 120-2, and third path 120-3 (individually or collectively referred to as "path 120" or "paths 120"), when propagating from the transmitter to the receiver. For example only, a portion of the transmitted radio signal may follow the shortest path (first path 120-1) from the transmitter radio device 110-1 to the receiver radio device 110-2. This first path 120-1 may be referred to as the "line-of-sight" (or "LOS") path. Other portions of the transmitted radio signal may follow different paths 120-2, 120-3 through the space 105. It should be appreciated that, although FIG. 1 illustrates three example paths 120 (first path 120-1, second path 120-2, and third path 120-3), there may be fewer or more paths 120, including paths 120 arranged in a "continuous band."

As the transmitted radio signals travel from the transmitter radio device 110-1 to the receiver radio device 110-2, they may be reflected off, and/or scattered and/or diffracted from, and/or attenuated by objects 140 (walls, windows, doors and furniture, people, pets, and the like) in the space 105. Different portions of the transmitted radio signal that travel along different spatial paths 120 may be attenuated and phase-shifted or time-shifted relative to other portions of the signal. Further, different portions of the transmitted radio signal that travel along different spatial paths 120 may be attenuated and phase-shifted or time-shifted differently if an object 140 moves, a person breathes, a heartbeats, or there is some other change somewhere nearby or along that spatial path 120. At least some portion of the transmitted radio signals may be received and processed at the receiver radio device 110-2. The received signal may be analyzed to determine information related to the environment (space 105) experienced by the radio signals. In this disclosure, analyzing received radio signals to determine information related to the environment experienced by the radio signals may be referred to as environmental signal extraction ("ESE").

The transmitted and received radio signals can be expressed as functions x(t) and y(t), respectively. In some aspects, the received signal y(t) can be mathematically modeled as y(t)=h(t)*x(t)+n(t), where n(t) is a noise term and h(t) is the channel response (CIR). In this example, the received radio signal y(t) has experienced the space 105 by traveling through it and, by analyzing the channel response (h(t)), it may be able to determine information about the space 105. Such information can include, e.g., whether something was moving in the space 105, whether something was present in the space 105, breathing and how fast it was breathing in the space 105, and/or whether something with a heartbeat and the rate of the heartbeat was in the space 105.

Many techniques for using radio signals to probe a space 105 (radar, sounding, pinging, Doppler, etc.) can be used to generate channel responses that may be analyzed to detect changes in a space 105. For example only, the channel responses may be embedded in received signal amplitudes and/or phases and/or timing. Additionally or alternatively, the channel responses may be channel impulse responses (CIR), channel frequency responses (CFR), channel state information (CSI), received signal strength indications (RSSI), or any other type of channel response. Any suitable technique for extracting channel information from radio signals can be utilized in the sensor system 100 described herein. For ease of description, the term CSI may be used herein to generally refer to information related to the environment or space 105 that can be extracted from received radio signals.

As described herein, the transmitter radio device 110-1 may transmit a radio signal to the receiver radio device 110-2, which receives that transmitted signal. In some implementations, and as mentioned above, the receiver radio device 110-2 may subsequently transmit a second radio signal to the transmitter radio device 110-1, which receives that second signal. Each of the first and second radio signals can be reflected off, and/or scattered and/or diffracted from, and/or attenuated by objects 140 (walls, windows, doors and furniture, people, pets, and the like) in the space 105 as it "experiences the environment" of the space 105. The environment experienced by the radio signals may change when objects 140 and/or living beings in the environment are present and/or move in particular or detectable ways. Different portions of the transmitted signals may be attenuated and phase-shifted or time-shifted relative to other portions of the signals, and at least some portion of the transmitted signals may be received and processed. The received signals may be analyzed at either the transmitter radio device 110-1, the receiver radio device 110-2, or both the transmitter and receiver radio devices 110-1, 110-2 to determine information related to the environment (space 105) experienced by the radio signals.

It will be appreciated in light of the disclosure that transmitted radio signals can experience an environment in which at least one human is present, moves and/or breathes and/or has a heartbeat. As mentioned above, radio signals may be reflected off, and/or scattered and/or diffracted from, and/or attenuated differently when an object 140 (such as a human) is in one location rather than another, and/or when a person's chest expands or contracts to draw in or breathe out a breath, and/or when a vein and/or artery and/or patch of skin moves up and down (or in and out) with a person's heartbeat. A person that is sleeping and/or sitting still may still be changing the environment experienced by radio signals compared to the radio experienced when the environment had no humans present. A person that is sleeping and/or sitting still may also be changing the environment experienced by radio signals because their chest cavity moving in and out with each breath, which may affect the amplitude and/or phase and/or timing of radio signals traveling from one radio device to another. Additionally or alternatively, a person that is sleeping and/or sitting still but may still be changing the environment experienced by radio signals because some portion of their body is pulsating at their heart rate and these small movements may affect the amplitude and/or phase and/or timing of radio signals traveling from one radio device to another. A person may be hardly moving at all, moving normally, moving quite a bit, and/or moving in an abnormal way, which may change the environment experienced by radio signals because the person's movement may affect the amplitude and/or phase and/or timing of radio signals traveling from one radio device to another.

As radio signals travel through the space 105 they may experience an environment in which at least one human moves. The sensor system 100 can determine occupancy and at least one other parameter based on the detected movement, e.g., based on the transmitted and received radio signals. For example only, when the sensor system 100 determines that a human is breathing in a region but that there is little to no other movement detected, the sensor system 100 may determine that a human is present and is not moving. In further examples, the sensor system 100 may associate little or no movement for a period of time with a human being asleep. Additionally or alternatively, the sensor system 100 may associate a rapid movement of a human followed by little or no movement of a human with a human falling and/or being injured. The signal collection, extraction, processing, etc. disclosed herein can provide information in addition to human occupancy. The sensor system 100 can be used to monitor human motion, breathing, heartrate, and infer and/or predict and/or produce output signals that indicate the state of a human, the health of a human, changes to the state or health of a human, and other characteristics of a human or other object 140 in the space 105.

In some aspects, the sensor system 100 can individually recognize and sense different humans in the space 150. For example only, individuals may have different breathing rates and/or different heart rates and may be distinguishable by the sensor system 100. In further examples, different individuals may impact radio signals differently and may have a radio signature that may be recognized by the sensor system 100. For example only, certain humans may impact the amplitude and/or phase and/or timing of the radio signals in a way that is recognizable to any occupancy-centric algorithms running in the sensor system 100.

In some implementations, a human in a radio environment may gesture in certain ways that are recognizable to the sensor system 100. A human may raise their hand up and down, may turn a thumbs up to a thumbs down, may pretend to shiver, may fan themselves, or perform another gesture and the sensor system 100 may detect and recognize these gestures. The detected gestures can be included as features in the algorithm that determines if a certain control system (e.g., HVAC system) in the space 105 should be adjusted. For example only, a human in the space 105 may wave their hand like a fan and the sensor system 100 may recognize that gesture and send an output signal to a thermostat or air conditioning/cooling unit to reduce the temperature in the space 105. It should be appreciated that a variety of gestures could be detected and used to initiate steps that could be taken to control, adjust, and/or vary heating, cooling, ventilation, security, lighting, power, entertainment systems, and other systems in or associated with the space 105.

In certain implementations, the space 105 can include a plurality of transmitter radio devices 110-1 and/or a plurality of receiver radio devices 110-2. For example only, two or more transmitter radio devices 110-1 may transmit radio signals to at least one receiver radio device 110-2. In further examples, two or more receiver radio devices 110-2 may receive radio signals from at least one of the transmitter radio devices 110-1. In yet another example, in specific implementations there may be two or more radio devices 110 capable of transmitting and receiving radio signals and any of these devices 110 may be transmitting and receiving signals to any other device 110 that are within range of said radio signals. In such implementations, the radio signals traveling in either or both directions between any transmitter radio device 110-1 and any receiver radio device 110-2 may be reflected off, and/or scattered and/or diffracted from, and/or attenuated by walls, windows, doors and furniture and other stationary objects, as well as by people and pets, and other mobile objects. Different portions of the transmitted signals may be attenuated and delayed relative to other portions of the signals, and at least some portion of the transmitted signals may be received and processed by at least one receiver radio device 110-2. The received signals may be analyzed at any, some, or all of the radio devices 110, or even remotely from the radio devices, e.g., at a centralized computing device or a remote computing device accessible via a network, to determine information related to the environment experienced by the radio signals. In some embodiments, the environment experienced by radio signals may change when objects and/or living beings are in the space 105 and/or move in particular or detectable ways.

A radio device 110 may also receive radio signals that are intended for other devices, which is referred to as "sniffing" the communications between other radio devices. The radio device 110 may analyze such "sniffed" signals to determine information related to the environment experienced by those radio signals. Similar to the radio signals intended for the radio device 110, the environment experienced by "sniffed" radio signals may change when objects 140 and/or living beings are in the environment and/or move in particular or detectable ways.

Additionally or alternatively, a radio device 110 may "ping" one or more other radio devices 110 to initiate the transmission of a data packet or data stream from the pinged radio devices 110. The pinging may be periodic or aperiodic and the timing of the pings may be a settable parameter that is set manually, automatically, and/or under software control. In some implementations, the settable parameter may be chosen and/or varied by the occupancy-centric algorithms or other algorithms running in the sensor system 100.

For example only, at least one radio device 110 may ping at least one other radio device 110 at least 10 times a second, at least 10 times a minute, at least 10 times an hour, at least 10 times a day, at least 10 times a week, and/or at least 10 times a month. Upon receiving a ping, the one or more other radio devices 110 may send a data packet and/or a data stream back to the pinging radio device 110. Upon receiving a ping, the one or more other radio devices may initiate the sending of a sequence of data packets and/or radio signals back to the pinging radio device 110. The sequence of data packets and/or radio signals may be transmitted over relatively short periods of time, or relatively long periods of time, or may persist until another ping indicates that transmissions from the pinged devices should stop. The pinging radio device 110 may analyze the sent data packet or packets and/or data stream or streams and determine parameters of the radio environment such as the space 105. Parameters of the radio environment may include but are not limited to, the distance between radio devices 110, the time of flight of radio signals, the angle of arrival of radio signals, standard deviations of amplitude and phase signals in the CSI, temporal and frequency correlations of amplitude and phase signals in the CSI, averages of amplitude and phase signals in the CSI, energy in the peaks of CSI amplitude and phase, the presence of objects 140 in the radio environment (space 105), the presence of moving humans, breathing humans, humans with heartbeats in the environment, the presence of moving animals, breathing animals, animals with heartbeats in the environment, the motion of objects 140 in the environment, and the presence of multiple humans and/or animals in the environment.

The radio signals exchanged between the transmitter radio device 110-1 and receiver radio device 110-2, may be detected and processed and amplitude and/or phase information may be extracted from some, all, or any portion of the detected and processed signals. The amplitude and/or phase information may be monitored and/or stored for some period of time. For example only, the stored information may be associated with a certain pair of transmitter radio device 110-1 and receiver radio device 110-2, a certain transmitter receiver antenna pair, a time or period of time, a certain location or region, a certain day or period of days, a certain temperature or range of temperatures, the tripping of a monitor or sensor signal, and/or the engagement of at least one piece of equipment or a control system in the vicinity of the radio signals. The stored information may be associated with commands that may be received from remote devices, control devices, system input devices and the like. Changes in the amplitude and/or phase and/or timing information derived from the radio signals may be associated with changes in the environment (space 105) experienced by the radio waves.

In some aspects, additional processing of the amplitude and/or phase information may be performed by firmware, software programs, algorithms, processors, code, scripts, and the like, which provide additional processing capabilities to those available as part of the standardized, customized, or proprietary communications protocol. For occupancy sensing applications, this additional processing may be referred to as occupant processing, occupancy-centric processing, occupancy-finding processing or similar, which may be performed based on occupant algorithms, occupancy-centric algorithms, or similarly named algorithms. Such processing techniques and algorithms may utilize signals produced by commercial or other chipsets and analyze them to determine whether changes in the standard signals or information derived therefrom should be interpreted as an occupant or multiple occupants being in a space 105.

Radio signals may comprise one or more carrier signals. In some protocols, multiple carriers may be referred to as subcarriers or subcarrier groups. In some implementations, any or all of the subcarriers or subcarrier groups may be received and processed as described herein and the impact of the environment on those subcarrier signals or groups may be different. For example only, each subcarrier in a radio signal may have a different center frequency and the environmental parameters influencing radio signal propagation may be frequency dependent. Additionally or alternatively, the amplitude and phase or timing, and/or the change in the amplitude and phase or timing, due to the presence of humans or objects 140 in the space 105 may be different. It should be appreciated that any, some, or all of the subcarrier signals or groups may be used to extract information about the environment (space 105) experienced by radio signals. In some implementations, the number of analyzed subcarriers or groups and which subcarriers or groups are analyzed may be a settable parameter that can be set manually, automatically, and/or under software control, e.g., the parameter may be chosen and/or varied by occupancy-centric algorithms or other algorithms running in the sensor system 100.

Figure 3:
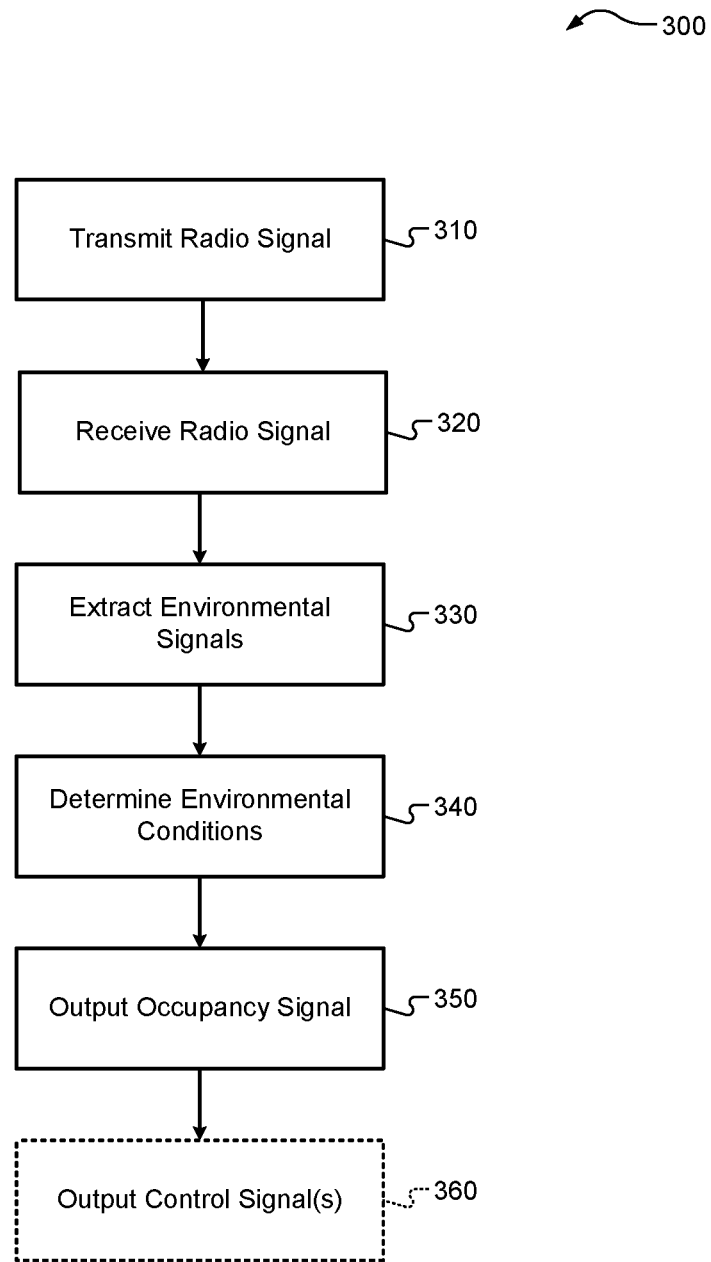
FIG. 3 is a flow diagram of an example technique for sensing occupancy in a space according to some implementations of the present disclosure.

With additional reference to FIG. 3, a flowchart of an example processing method 300 is illustrated. It should be appreciated that the method 300 is merely an example and that, in some implementations, the present disclosure may not be limited to the exact method illustrated, and that the method steps, processes, and operations described herein are not to be construed as necessarily requiring their performance in the particular order discussed or illustrated, unless specifically identified as an order of performance. It is also to be understood that additional or alternative steps may be employed, as the identified processing steps may be reordered or omitted depending on the desired implementation. The processes identified may or may not be performed in separate chips or hardware components and may or may not be performed using separate or distinct programs, algorithms, processors, code, and scripts. Additionally, the method 300 can be performed by the disclosed sensor system 100, which can include a radio device 110 alone, a plurality of radio devices 110 working in combination, or one or more radio devices 110 working in combination with one or more other devices. For the sake of simplicity, however, the description herein will be directed to the method 300 being performed by the sensor system 100 even though individual operations may be performed by a radio device 110 alone, a plurality of radio devices 110 working in combination, or one or more radio devices 110 working in combination with one or more other devices in the sensory system 100.

At 310, a radio signal can be transmitted, e.g., by a radio device 110 such as the transmitter radio device 110-1 described herein. The transmitted radio signal will propagate through the environment (the space 105) be received at 320, e.g., by a radio device 110 such as the receiver radio device 110-2. The received radio signal may have experienced the environment in the vicinity of one or both of the radio devices. The extent or range or spatial dimensions of the environment experienced by the radio signals may be determined by any of, or any combination of, the power of the transmitter, the sensitivity of the receiver, the attenuation of radio signals in the environment, the signal to noise ratio of the received signal, the speed or data rate of the transmitted signals, the modulation format of the radio signals, the data rate of the radio signals, the composition and size of the materials and objects 140 in the radio environment, the signaling protocol being used, the frequency of the transmitted signal, the processing algorithms and the parameters of the processing algorithms in the receiver, and the like.

The radio devices 110 may communicate with each other using any suitable signaling protocol. In one aspect, the radio devices 110 may communicate with each other using WiFi signaling protocols. Additionally or alternatively, the radio devices 110 may communicate with each other using standardized signaling protocols, such as Bluetooth™, ZigBee™, 5G, ultrawideband (UWB), any of the IEEE standards including but not limited to IEEE 802.11, IEEE 802.15.1, IEEE 802.15.3 IEEE 802.15.4, IEEE 802.16, IEEE IMT-Advanced/3GPP, Long Term Evolution (LTE), and/or NFC (near field communication). Further, in some implementations, the radio devices 110 may communicate with each other using proprietary signaling protocols and/or customized signaling protocols. In other aspects, the radio devices of this disclosure may communicate with each other using signaling protocols that include data packets, frames, sequences and the like that may be utilized by the receiver radio device 110-2 to extract channel information from the signals. Radio devices 110 may be able to extract signal amplitude, phase and timing information by analyzing received data packets, frames, sequences, or other signal characteristics. In embodiments, the information derived from the radio signals may be associated with changes in the environment experienced by the radio waves.

In yet further examples, the radio devices 110 may communicate with each other using WiFi signaling protocols and the receiver radio device 110-2 may generate channel information (which is sometimes referred to as channel state information, or "CSI"). In the WiFi protocol, CSI may be determined from the analysis of "sounding frames" in 802.11ac packets and may be used to characterize how radio signals are reflected and scattered by occupants and objects 140 in a space 105. In some aspects, CSI may be determined by analysis of a preamble of one or more WiFi packets. Alternatively or additionally, CSI may be determined from the data packet and/or from portions of the data packet. Furthermore, CSI may be determined from analysis of the data packet frames, from long and/or short preambles or multiple preambles, applicable symbols from long training fields (LTFs) and/or multiple LTFs, and/or from any type of training data, signals, frames or other feature(s) of data packet(s).

In some aspects, signal processing can be performed on some or all of the determined CSI data. For example only, noise may be removed or reduced in the CSI data. Techniques such as phase offset removal, which may remove sampling time offsets and/or sampling frequency offsets, and/or carrier frequency offsets, may be utilized. Techniques such as outlier removal using techniques such as moving averages, filtering, nulling, and the like may be used.

The sensor system 100 of the present disclosure may implement an occupancy-centric algorithm 250. In this disclosure, the term "occupancy-centric" means that the software, programs, codes, files, processing, and other data have been developed and/or are being utilized to determine human occupancy in a certain radio environment by analyzing radio signals that have experienced that radio environment. Although FIG. 2 illustrates the occupancy-centric algorithm 250 as being part of or implemented in a radio device 110, it should be appreciated that the occupancy-centric algorithm 250 can be implemented in more than one radio device 110, in one or more radio devices 110 working with one or more other devices, or in any other components of the sensor system 100. In embodiments, one radio device 110-1 may be an access point and another radio device 110-2 may be a computer. The access point may ping the computer and the computer may send wireless signals to the access point in response to the ping. The access point may process the received signals and input them to an occupancy-centric algorithm 250, which may be used to analyze the signals to determine whether one or more humans are in the space 105. In embodiments, analyzing the signals may include looking for one or more features in the signals and based on the presence or strength of the one or more features outputting a signal that indicates one or more humans or no humans in the space 105. In embodiments, the computer may be sending or broadcasting wireless signals without receiving a ping and the access point may analyze the signals as described herein. In embodiments, the roles of the access point and computer may be reversed so that the computer can run the occupancy-centric algorithm 250 and can generate a signal or output signal that is indicative of the presence of one or more humans. In embodiments, the access point may run the occupancy-centric 250 algorithm and send a signal to the computer and the computer may generate a signal or our output signal that is indicative of the presence of a human. In embodiments, the occupancy-centric algorithm 250 may run on a third device or on a third radio device 110-3. In various embodiments, some or all of the radio devices may have some or all of the processor 113, memory 115, input device 117, output device 119 and occupancy-centric algorithm 250. By way of these examples, radio devices 110-1 and 110-2 may be similar devices, the same model devices, different devices, devices with a primary purpose that is not related to occupancy detection but whose wireless communication capabilities and any other capabilities described herein may be used as part (alone or in combination) of the sensor system.

The occupancy-centric algorithm 250 may analyze the CSI data and/or the processed CSI data that is generated by commercial chipsets and/or commercial WiFi equipment. In order to implement the occupancy-centric algorithm 250, various modifications to the radio devices 110 may be made. For example only: (i) commercial chipsets and/or commercial WiFi equipment may be operating using firmware and/or drivers other than what was factory installed for realizing standardized communications protocols in order to support some or all portions of the occupancy-centric algorithms described in this disclosure; (ii) in some aspects, certain chips and/or circuits in radio devices may have to be re-flashed or loaded with firmware, drivers and/or software other than what was factory installed by the original equipment manufacturer (OEM) in order to support some or all portions of the occupancy-centric algorithms described in this disclosure; (iii) source code developed to implement data retrieval for occupancy sensing may need to be installed in commercial radio equipment in order to implement the sensor system 100; (iv) occupancy-centric binary files and/or occupancy-centric driver files may need to be uploaded to some or all of the radio devices 110; (iv) firmware including but not limited to OpenWrt™ firmware may need to be uploaded to some or all of the radio devices 110; (vi) some portion or all of the memory of at least one updateable component in any of the radio devices 110 may be overwritten with occupancy-centric code; (vii) Ubuntu may need to be running on at least one of the radio devices 110 and/or Ubuntu versions that are not the most current version of Ubuntu may need to be running on at least one of the radio devices 110; and/or (viii) any, some or all of the radio devices 110 in a sensor system 100 may need to be rebooted before they may operate as described herein.

Typical commercially available WiFi devices do not automatically provide access to ("expose") CSI data for analysis by third party machine code, firmware, software, and/or processing algorithms. In some aspects, such CSI data can be made accessible by re-flashing updateable components and/or uploading new drivers and/or binary files that have been developed to access and analyze the determined CSI data. Such firmware, binary files, drivers, etc. can be characterized as occupancy-centric if they have been developed to expose CSI information to be used in the sensor system 110.

The various tasks associated with the signal reception, analysis, processing, generation, manipulation, averaging, filtering, thresholding, etc. described throughout this disclosure may be implemented in machine code and/or firmware and/or using computer languages such as C™, C++™, Python™, and the like. For example only, information for tasks associated with the signal reception, analysis, processing, generation, manipulation, averaging, filtering, thresholding, etc. may reside in the memory 115, which can take the form of any or any combination of binary files, drivers, RAM, non-volatile RAM, EPROMs, short term memory, long term memory, caches and/or any type of known memory or information files.

In various implementations, the occupancy-centric algorithm 250 may extract environmental signals from the radio signal(s), which is referred to herein as environmental signal extraction ("ESE"). Extracted environmental signals may include, but are not limited to, amplitude of the radio signals, phase of the radio signals, timing of the radio signals, energy, and/or power of the radio signals. The extracted environmental signals may be related to an entire radio signal and/or to portions of the radio signals. For example only, in WiFi embodiments, environmental signals may be extracted from the data packet and/or from portions of the data packet. In other aspects, environmental signals may be extracted from analysis of the data packet frames, from long and/or short preambles or multiple preambles, applicable symbols from long training fields (LTFs), from any type of training data, signals, frames, or any suitable portion or portions of the radio signal. Further examples include analyzing one, some, or all of the subcarrier signals, e.g., amplitude only, phase only, or both amplitude and phase information on one, some, or all of the subcarriers may be analyzed.

In various implementations of the present disclosure, the occupancy-centric algorithm 250 may compare CSI generated at one time to CSI generated at another time. The occupancy-centric algorithm 250 may compare: (i) CSI generated from one packet to CSI generated from another packet; (ii) CSI generated from one transmitter/receiver pair to CSI generated from another transmitter/receiver pair; (iii) CSI generated from one transmitter/receiver antenna pair to CSI generated from another transmitter/receiver antenna pair; (iv) CSI generated from one or some subcarriers to CSI generated from one or some other subcarriers; (v) CSI generated from one transmitter/receiver pair to stored CSI; (vi) unprocessed CSI generated from one transmitter/receiver pair to processed CSI; (vii) CSI generated at one place to CSI generated at another place; (viii) CSI generated at one time to CSI stored in a buffer, or file, or database, or short term or long-term memory unit, or any other storage device or media (memory 115); (ix) CSI generated between a first device and a second device to CSI generated between a second device and a first device; (x) CSI generated between a first device and a second device to CSI generated between a second device and a third device; and/or (xi) CSI generated between a first device and a second device to CSI generated between any other two or more devices.

The occupancy-centric algorithm 250 may process some, most, or all of the generated CSI data. In certain aspects, the occupancy-centric algorithm 250 may apply weights to different portions of the CSI data so that certain portions of the data may have a relatively bigger or smaller impact on the outcome of the occupancy-centric processing. Furthermore, the occupancy-centric algorithm 250 may adjust which portions of the CSI data are analyzed, which portions are weighted, and what the weights are. The occupancy-centric algorithm 250 may associate any, some, or all of the variables or changes in the variables described herein with human occupancy in a space 105 (such as a room or a home).

In certain implementations, the occupancy-centric algorithm 250 may average some, most, or all of the CSI data. Further, the occupancy-centric algorithm 250 may process amplitude and phase data separately using the same, similar, or different processing steps and variables. For example only, the occupancy-centric algorithm 250 may compute an average phase, time, amplitude, energy, phase change, time change, amplitude change, energy change, phase spread, time spread, amplitude spread, energy spread, phase change spread, time change spread, amplitude spread change, and energy spread change. The occupancy-centric algorithm 250 may associate any, some, or all of the variables or changes in the variables described herein with human occupancy in a space 105 (such as a room or a home). For example only, the occupancy-centric algorithm 250 may associate an increase in an average phase signal and a decrease in an average amplitude signal with the presence of a human. In further examples, the algorithm may associate a change in the phase value calculated for subcarrier channel 33 with the presence of a human. The occupancy-centric algorithm 250 may adapt and change under machine learning or artificial intelligence control. In embodiments, the occupancy-centric algorithm 250 may be a machine learning algorithm configured to be deployed to analyze individual and/or combined signals across spatial (different antennas), temporal and frequency domains. In embodiments, features of the signals can include, but not limited to, power, angle of arrival, direction of arrival, time of flight, time of arrival, time of flight, time difference of arrival, received signal strength, fading, signal-to-noise-ratio, amplitude and phase of subcarriers, differences in amplitude and phase as a function of time, space (antenna) and frequency (compared across subcarriers). In embodiments, features of the signals that can be analyzed can also include changes to the features including abrupt changes may be analyzed to look for patterns or signatures that have been determined indicate the presence of one or more humans in the environment 105. In embodiments, the occupancy-centric algorithm 250 may identify certain features extracted from the radio signals as being more or especially indicative of human presence and may assign weights to different features when determining whether or not a human is in the space 105.

In embodiments, the occupancy-centric algorithm 250 may adapt and change based on signals input to an input device 117. The system 100 performance may be improved by changes to the machine learning algorithm and/or to the weights assigned to certain features. Users and/or occupants may input occupancy information to the input device 117 and the output from the occupancy-centric algorithm 250 may be checked for accuracy against the input occupancy information. The occupancy-centric algorithm may be adapted or changed to improve human detection accuracy and overall system performance. In embodiments, other sensor information collected by the system 100 may indicate the presence of one or more humans in the space 105 and the occupancy-centric algorithm 250 may determine that there is no human present in the space 105. The radio device 110 may use the output device 119 to send a signal to a user and/or occupant and/or other sensor and/or other device and/or network requesting additional information be sent to the radio device via a communication device 111 and/or an input device 117. The additional information may be used to alter or tune the occupancy-centric algorithm 250 to improve its performance.

In embodiments, the radio device 110 may use the output device 119 to send a signal to a user and/or occupant and/or other sensor and/or other device and/or network on a schedule, periodically, on demand, whenever a user interacts with a system, based on a threshold crossing or some internal performance metric. In embodiments, an output device 119 may flash a light to indicate the system needs user or occupant input. A user and/or occupant may approach a radio device and see questions on a display such as "were you home at 10 AM". The user and/or occupant may press a button to touch a screen to indicate whether the answer to the question is yes or no or not sure. In further examples, the output device 119 may send a message to one or more users' and/or occupants' cell phones or email accounts with a set of questions. The user and/or occupant may provide information in the form of answers to those questions by sending a message or electronic communication to the communication device 111 and/or input device 117 of the radio device and the radio device may use the information to adapt and/or change the occupancy-centric algorithm 205. In embodiments, the radio device may determine and store performance data and not make changes to the occupancy-centric algorithm until a certain amount of time has passed or a certain number of measurements have occurred or a certain amount of information has been received.

The occupancy-centric algorithm 250 may also use data from other sensors in the sensor system 100 to determine occupancy. Examples of such other sensors can include carbon dioxide ($CO_2$) sensors, passive infrared (PIR) sensors, ultrasonic and/or sound sensors, image/visual sensors, motion sensors, and electronic device sensors. In various aspects, the occupancy-centric algorithm 250 may collect information from smart home devices such as smart lights, smart doorbells and/or may collect power and/or usage information from appliances such as displays, computers, phones, smartphones, personal assistants, televisions, lights, refrigerators, coffee machines, water heaters, thermostats, air conditioners, game consoles, washing machines, and the like, and use some, most or all of that data to help determine occupancy of a space 105. The occupancy-centric algorithm 250 may use data that is input manually, such as through a button, dial, knob, keyboard, touchscreen, mouse, capacitive sensor, or resistive sensor. Additionally or alternatively, the occupancy-centric algorithm 250 may use data input through an electronic interface, a wireless interface, an optical interface, a computer interface, a network interface, or any type of interface used to send data or signals between people and devices or between devices and other devices.

The occupancy-centric algorithm 250 may include parameters that may be set manually, automatically, and/or under the control of another algorithm, processor, sensor, or other devices. Such adjustable parameters can include, but are not limited to, how often CSI data are collected, which CSI data are processed, which processing steps are running, and which data are output from the algorithm, although other parameters are within the scope of the present disclosure. In some implementations, the performance of the occupancy-centric algorithm 250 may be adjusted to conform to certain performance metrics, such as to minimize or reduce energy consumption, minimize or reduce required computation power/cycles, maximize or increase sensitivity, maximize or increase accuracy, or the like. A radio device running the occupancy-centric algorithm 250 may detect other devices in the sensor system 100 and may hand-off some or all processing and/or algorithm tasks to such other devices. For example only, processes and/or tasks may be handed off to other devices or distributed to multiple devices to extend battery lifetime of some device or devices, reduce power consumption of some device or devices, and/or to take advantage of faster processors or more efficient processors.

In some example implementations, a radio device 110 that uses WiFi signaling protocols may generate the so-called received signal strength indicator ("RSSI") signal. In the WiFi protocol, RSSI may be determined from the analysis 802.11 packets and may be used to characterize how radio signals are reflected and scattered by occupants and objects 140 in a space 105. The occupancy-centric algorithm 250 may analyze the RSSI data generated by commercial chipsets or commercial WiFi equipment, and/or may analyze the RSSI data that has been generated, processed, analyzed by and/or has utilized occupancy-centric machine code and/or firmware and/or drivers and/or binary files.

For example only, the occupancy-centric algorithm 250 may compare: (i) RSSI generated at one time to RSSI generated at another time; (ii) RSSI generated at one place to RSSI generated at another place; (iii) RSSI generated at one time and/or from one packet or a set of packets to RSSI generated at another time and/or another packet, and/or another set of packets; (iv) RSSI generated at one time to RSSI stored in a buffer, or file, or database, or short term or long-term memory unit, or any other storage device or media (memory 115); (v) RSSI generated between a first device and a second device to RSSI generated between a second device and a first device; (vi) RSSI generated for one, some or all of the subcarriers or groups of a radio signal to RSSI generated for one, some or all of the subcarriers or groups of a second radio signal.

Furthermore, the occupancy-centric algorithm 250 may process some, most, or all of the generated RSSI data. In some aspects, the occupancy-centric algorithm 250 may apply weights to different portions of the RSSI data so that certain portions of the data have a relatively bigger or smaller impact on the outcome of the occupancy-centric processing. The occupancy-centric algorithm 250 may also or alternatively adjust which portions of the RSSI data are analyzed, which portions are weighted and what the weights are, and/or may associate any, some, or all of the variables or changes in the variables described herein with human occupancy in a space 105.

The occupancy-centric algorithm 250 may average some, most, or all of the RSSI data. Additionally or alternatively, the occupancy-centric algorithm 250 may compute an average amplitude, energy, amplitude change, energy change, amplitude spread, energy spread, amplitude spread change, and/or energy spread change. Additionally or alternatively, the occupancy-centric algorithm 250 may compute a standard deviation or look for abrupt changes in signal amplitude, energy, amplitude change, energy change, amplitude spread, energy spread, amplitude spread change, and/or energy spread change. Any, some, or all of the variables described herein can be utilized by the occupancy-centric algorithm 250 to determine occupancy in the space 105. For example only, the occupancy-centric algorithm 250 may associate an increase in an average energy signal and a decrease in an energy spread signal with the presence of a human. In further examples, the occupancy-centric algorithm 250 may associate a change in the amplitude value calculated for subcarrier channel 33 with the presence of the human. The occupancy-central algorithm 250 may be adapted based on combinations of machine learning, artificial intelligence and user input.

In embodiments, the occupancy-centric algorithm 250 may use data from either CSI data or RSSI data, or both CSI and RSSI data, or any combination of data from the CSI and RSSI determined for WiFi packets, frames, communications and the like to determine occupancy. In some aspects, other data determined by the communication protocol may be analyzed and used to indicate the presence of a human or a moving object 140 or an animal and the like in a space 105. For example only, some communication protocols generate channel frequency response ("CFR") data and/or channel impulse response ("CIR") data, which can be used as described herein for CSI and/or RSSI data. Any combination of CFR, CIR, CSI, and RSSI data may be used by the occupancy-centric algorithm 250. Non-limiting examples include: (i) only CFR data may be used, (ii) only RSSI data may be used, and (iii) some combination of CFR data along with an ultrasonic detector can be used. It should be appreciated that any type or quantity of data that can be analyzed, processed, etc. to determine occupancy can be input to the occupancy-centric algorithm 250, and any combination of the sensor data, other sensor data, user inputs, control data, and/or analyzed data outputs may be used in the sensory system 100 described herein.

In embodiments, the occupancy-centric algorithm 250 may use additional data available from analyzing radio signals exchanged between radio devices 110. Such data may include data related to signal power, distance between a transmitter radio device 110-1 and a receiver radio device 110-2, time of flight signals, time difference of flight signals, angle of arrival of signals, time of arrival of signals, and time difference of arrival of signals. In aspects, the occupancy-centric algorithm 250 may use processing techniques and algorithms used in computer vision and image processing, especially when CSI is stored in 3D matrix representations, although other algorithms, such as the multiple signal classification (MUSIC) algorithm, may be used to analyze CSI in the sensor system 100. For example only, CSI may be processed and/or analyzed and/or compared using cross-correlation techniques. In various implementations, two CSI matrices may be cross correlated and the output of the cross correlations may be a measure of how similar or different two matrices are and may be part of determining whether a radio environment (space 105) is staying substantially the same or is changing.

In some aspects, one or more threshold values may be set for one of more measured and/or analyzed data values. Computed and/or analyzed and/or generated values that exceed a threshold level and/or are below a threshold value and/or are between a set of threshold values may be an indication of occupancy in a space 105. For example only, a radio device 110 may send an output occupancy signal and/or a decision output signal to another radio device 110 and/or a control system to indicate that a space 105 is occupied. The control system may perform some action upon receiving an occupancy and/or decision output signal. In other implementations, a control system may perform some action upon receiving an occupancy and/or decision output signal and at least one other control and/or sensor and/or occupancy and/or decision signal, where the at least one other control signal may be a signal from any, or any combination of, another sensor and/or monitor, a user input, a timer, a buffer or database containing other occupancy signals, or any other suitable device.

In some aspects, a single radio device 110 may operate as a hub in a sensor system 110. The radio device 110 operating as the hub may include the hardware and/or software that is used to execute/implement the occupancy-centric algorithm 250 (as shown in FIG. 2). In some implementations, the hub radio device 110 may also include the hardware and/or software that is used to execute and/or communicate with a control loop that may control one or more devices and/or systems, e.g., via network 200. A hub radio device 110 may communicate with one or more other radio devices 110 in the sensor system 100, e.g., it may receive communication and/or decision signals from another radio device 110 that includes the hardware and/or software that is used to execute the occupancy-centric algorithm 250.

The sensor system 110 may comprise more than one hub radio device 110. In such implementations, data analysis, occupancy determination, and system control may be performed in a single radio device 110 and/or in the hub radio device 110. In other implementations, data analysis, occupancy determination, and system control may be performed in a distributed fashion, with one or more radio devices 110 responsible for the execution of one or more steps in the control loop.

Referring again to FIG. 3, the sensor system 100 can include extracting environmental signals 330 from the radio signals. The environmental signal extraction can include processing received signals and determining CSI, RSSI, CFR, CIR and the like on any portion of the received signal. Further, environmental signal extraction may include processing any, all, or a combination of CSI, RSSI, CFR, and CIR from a single packet, multiple packets, a single transmitter/receiver pair, multiple transmitter/receiver pairs, multiple transmitter/receiver antenna pairs, a single transmitter/receiver subchannel, multiple transmitter/receiver subchannels, or any other combination of signals/devices. In aspects, environmental signal extraction may include comparing measured data to data thresholds, data inputs, user inputs, other sensor inputs, previously measured data and the like. Further, in some aspects, environmental signal extraction may include: (i) generating an output signal that may be an indication of human presence in the space 105; (ii) engaging a control loop and or a controlled or controllable system in a space 105 and operating that system in a way that is comfortable for human occupants. For example only, an output signal and/or decision output signal may indicate that humans are present. An output signal may be a temperature setting or a range of temperature settings that a heating/cooling system should attain in the space 105. An output signal may be a signal that is suitable for input into another data analysis stage, processing stage, signal extraction stage, signal determination stage, or similar control or analysis system.

At 340, the sensor system 100 can determine environmental conditions in the space 105 for the extracted environmental signals. Such environmental conditions determination can include processing any, all, or a combination of CSI, RSSI, CFR, and CIR from a single packet, multiple packets, a single transmitter/receiver pair, multiple transmitter/receiver pairs, multiple transmitter/receiver antenna pairs, a single transmitter/receiver subchannel, multiple transmitter/receiver subchannels, or any other combination of signals/devices. The environmental condition determination 340 may include comparing generated parameters and/or values to user settable parameters and/or values, stored parameters and/or values, calculated parameters or values, or any combination thereof. The parameters and/or values to which the generated parameters and/or values can be compared may change or otherwise variable. In embodiments, environmental determination may output a signal or signals that are related to a radio environment.

At 350, the sensor system 100 can output an occupancy signal that represents, contains data representing, or is otherwise indicative of the occupancy in the space 105. In some aspects, the occupancy signal indicates that a human is present, that more than one human is present, that a certain number of humans are present, that an animal is present, that a window has opened, that a door has opened, that at least one person is present but not moving, that a person has fallen, that a person has moved to a different space 105, or any other condition of the space 105 determined at 340.

In some aspects, the sensor system 100 may output the occupancy signal (and/or control signals based on the occupancy signal at 360) to systems that control the space 105 experienced by the radio signals. For example only, the sensor system 110 may provide the occupancy and/or control signals to heating, cooling, ventilation, security, lighting, power, and entertainment systems associated with the space 105. Such heating systems may receive occupancy and/or control signals from the sensor system 100 and may increase, decrease, or maintain the amount of heat supplied to the space 105. Similarly, cooling systems may receive occupancy and/or control signals from the sensor system 100 and may increase, decrease, or maintain the amount of cooling supplied to the space 105; ventilation systems may receive occupancy and/or control signals from the sensor system 100 and may increase, decrease, or maintain the amount of ventilation supplied to the space 105. Security systems may receive occupancy and/or control signals from the sensor system 100 and may turn on or turn off or leave security systems in their current state. Lighting systems may receive occupancy and/or control signals from the sensor system 100 and may increase, decrease, or maintain the amount of light supplied to the space 105. Power systems may receive occupancy and/or control signals from the sensor system 100 and may increase, decrease, or maintain the amount of power supplied to the space 105. As yet another example, entertainment systems may receive occupancy and/or control signals from the sensor system 100 and may increase, decrease or maintain the volume, channel, settings and the like of any audio, video and/or other entertainment signals supplied to the space 105.

In certain implementations, the sensor system 100 may provide output control signals and/or information that are part of a system control feedback loop. The sensor system 100 may supply control signals at rates no less than 10 times a second, no less than 10 times a minute, at rates no less than 10 times an hour, at rates no less than 10 times a day, at rates no less than 10 times a week, and/or at rates no less than 10 times a month. The sensor system 100 may, in various implementations, provide multiple output signals based on the analysis of multiple radio signals. In embodiments, the sensor system 100 may provide output signals based on the analysis of radio signals and input from any of the other types of sensors described in this disclosure.

A control loop may control one of any or a combination of phones, computers, tablets, watches, speakers, thermostats, heating devices, cooling devices, ventilation devices, lighting devices, power stations, chargers, home appliances, routers, access points, models, e-readers, and/or personal assistants (e.g. Google Home, Amazon Echo, Apple HomePod). A control loop may also control some, none, or any of a combination of heating, cooling, ventilation, security, lighting, power, and entertainment systems.

In embodiments, one radio device 110 may request other radio devices 110 to send data that has been extracted from radio signals received by those other radio devices. For example, a first radio device may request a second radio device to send CSI, RSSI, CFR, CIR, time of arrival, time difference of arrival, signal power, angle of arrival, and/or distance information for signals traveling between the first radio device and at least a second device or between the at least one second device and at least a third device.

According to one example, the sensor system 100 may comprise at least two radio devices 110 where at least one radio device 110 may analyze, or may communicate with a device that analyzes data from at least one radio communication link and at least one radio device 110 may provide control signals to control systems or devices in a space 105 in response to data collected from the at least one communication link.

In further examples, the sensor system 100 may comprise at least two radio devices 110 where at least one radio device 110 is integrated in a thermostat or smart thermostat. The thermostat or smart thermostat may analyze, or may communicate with a device that analyzes, data from at least one radio communication link and the thermostat or smart thermostat may provide control signals to control the HVAC systems in a space 105. A smart thermostat may comprise some, any or all of the hardware, software, firmware and drivers to perform one, some or any of the environmental signal extraction 330, environmental determination 340, and output 350, 360 of the present disclosure.

In embodiments, data analysis and calculation of the control parameters may be performed remotely, such as on a shared computer or server in communication with one or more radio devices 110. The results of data analysis and control parameter determination may be transmitted over a wired communications link, over a primarily electrical wire communications link, over a primarily optical link, over a primarily wireless link, or over a link that is some combination of wired and wireless and may include intermediate switches, routers, access point, data format conversions and the like.

The sensor system 110 may include a thermostat comprising a radio device 110-1 and at least a second radio device 110-2. The thermostat may receive wireless communication or information signals from the at least one second radio device 110-1 and may analyze these signals to obtain values or parameters associated with the environment experienced by the communication or information signals (space 105). The thermostat may store these values or parameters and/or run the occupancy-centric algorithm 250 that may analyze these values or parameters to determine whether the space 105 includes one or more humans. The thermostat may adjust heating, cooling and/or ventilation systems in the home based on whether or not a human is present. For example, if a human is present, the thermostat may adjust the heating, cooling and/or ventilation levels to levels determined to be comfortable for human occupied spaces. In embodiments, the levels determined to be comfortable for human occupied spaces may be occupancy-specific, room-specific, area-specific, building-specific, time-specific, outdoor temperature specific, season-specific, location-specific, energy-price specific, energy source specific and the like. If the data analysis determines that an occupant is not present, the thermostat may set the heating, cooling and/or ventilation levels to levels that conserve energy (setback temperature and ventilation settings).

In yet another example embodiment, the sensor system 100 may include a thermostat comprising a transmitter radio device 110-1 and at least one receiver radio device 110-2. The at least one receiver radio device 110-2 may receive wireless communication or information signals from the thermostat and may analyze these signals to obtain values or parameters associated with the environment experienced (the space 105) by the communication or information signals. The at least one receiver radio device 110-2 may store these values or parameters and/or run the occupancy-centric algorithm 250 that may analyze these values or parameters to determine whether the space 105 includes humans. The at least one receiver radio device 110-2 may send the determined values or parameters to the thermostat. The at least one receiver radio device 110-2 may tell the thermostat that one or more humans are present or the at least one receiver radio device 110-2 may send data to the thermostat that the thermostat may analyze to determine whether or not one or more human is present. The thermostat may adjust heating, cooling and/or ventilation systems in the home based on whether or not a human is present, as described herein.

According to additional implementations, the sensor system 100 may include a thermostat comprising a transmitter radio device 110-1 and at least one receiver radio device 110-2. The at least one receiver radio device 110-2 may receive wireless communication or information signals from the thermostat and may analyze these signals to obtain values or parameters associated with the environment experienced by the communication or information signals. The at least one receiver radio device 110-2 may store these values or parameters and/or run the occupancy-centric algorithm 250 that may analyze these values or parameters to determine whether the environment includes one or more humans. The at least one receiver radio device 110-2 may send the determined values or parameters to the thermostat. The at least one receiver radio device 110-2 may tell the thermostat that one or more humans are present or the at least one second device may send data to the thermostat that the thermostat may analyze to determine whether or not one or more human is present. The thermostat may use additional sensor inputs, user inputs, or any other types of data or information disclosed in this disclosure to determine whether an occupant is in a space and whether adjustments should be made to the heating, cooling and/or ventilation levels in the room, area, and/or building (space 105).

Any of the example sensor systems 100 described herein may include at least another radio device 110 ("third radio device") in addition to the transmitter radio device 110-1 and the at least one receiver radio device 110-2. The third radio device 110 may be physically collocated with either the thermostat or the receiver radio device 110-2. The third radio device 110 may be integrated into the same electronic device, package, box, or system as the thermostat or the receiver radio device 110-2, or may be physically separate or remote from the thermostat and/or the receiver radio device 110-2. The third radio device may generate and/or receive wireless communication or information signals from the thermostat and/or the receiver radio device 110-2 and may analyze these signals to obtain values or parameters associated with the environment experienced by the communication or information signals. The third radio device may store these values or parameters and/or run the occupancy-centric algorithm 250 that may analyze these values or parameters to determine whether the environment includes one or more humans. The third radio device may send the determined values or parameters to the thermostat and/or the receiver radio device 110-2. The receiver radio device 110-2 or the thermostat or both may run the occupancy-centric algorithm 250 to determine whether a human is present in the room and/or area and/or building near to or enclosing the thermostat, receiver radio device 110-2, and third radio device 110.

This disclosure contemplates that occupancy data can be collected and analyzed and occupancy determined by some or any of the radio devices 110 within communication range of each other. That is, determining occupancy may be a distributed process, with different devices performing different parts of the data collection, generation, analysis, thresholding, and other aspects of the method 300.

This disclosure contemplates that single or multiple radio devices 110 may communicate using single or multiple communication protocols. In aspects, these radio devices 110 may communicate with other devices using any or any combination of standardized signaling protocols such as WiFi, Bluetooth™, Zigbee™, 5G, ultrawideband (UWB), any of the IEEE standards including but not limited to IEEE 802.11, IEEE 802.15.1, IEEE 802.15.3 IEEE 802.15.4, IEEE 802.16, IEEE IMT-Advanced/3GPP, Long Term Evolution (LTE), NFC (near field communication), and the like. Devices may communicate using different radio frequency bands such as 5 GHz WiFi and 2.4 GHz WiFi. This disclosure contemplates that customized radio signaling schemes may be developed and that channel information extracted from these customized signaling schemes may also be used to realize this disclosure. This disclosure contemplates that proprietary radio signaling schemes may be developed and/or utilized and that channel information extracted from these proprietary signaling schemes may also be used to realize this disclosure.

This disclosure contemplates that the occupancy-centric algorithm 250 may change and evolve over time. The occupancy-centric algorithm 250 may be altered using training algorithms, learning algorithms, machine learning algorithms, artificial intelligence algorithms, and the like. In some aspects, the occupancy-centric algorithm 250 itself may include at least portions of what might be considered learning algorithms, training algorithms, machine learning algorithms, and/or artificial intelligence algorithms. Shallow learning algorithms, deep learning algorithms, deep neural networks, and the like may be utilized to improve performance of the sensor system 100 and/or occupancy-centric algorithm 250.

This disclosure contemplates that channel amplitude and/or phase and/or timing data derived from the communication of radio signals may not directly indicate the presence of humans in or nearby the radio channel. Data analysis and the occupancy-centric algorithm 250 may be necessary to associate channel amplitude and/or phase and/or timing data and/or changes in channel amplitude and/or phase and/or timing data with the presence of humans. Data analysis may require that multiple data frames are analyzed, multiple channels are analyzed, and the like. Trends in the changes of certain data signals may be indicative of human presence. The trends that indicate occupancy at one time may be different than the trends that indicate occupancy at another time. Therefore, this disclosure contemplates that the occupancy-centric algorithm 250 may change and evolve over time, either automatically or in response to some sort of external input(s). External input(s) may include, but is not limited to, other sensor data, user inputs, software upgrades, and other additional or different sensor devices.

In certain aspects, at least two radio devices 110 may communicate over a wireless channel that travels through an environment experienced by the radio signals such as the space 105. A first radio device 110 may ping the second radio device 110 a few times a second and the second radio device 110 may send one or more packets to the first radio device 110 in response to the ping. The first radio device 110 may receive the packet or packets from the second radio device 110 and process the packets to expose received amplitude and/or phase and/or timing information that is characteristic of the radio environment and/or channel. As mentioned herein, the terms "CSI" may refer to the amplitude and/or phase and/or timing information, but it should be understood that CSI is just one way of expressing the amplitude and/or phase and/or timing information that is characteristic of the channel or radio environment.

The received CSI may be a real number, a complex number, a combination of real and complex numbers and may be a vector of real and/or complex numbers and may be a two-dimensional or three-dimensional matrix of real and/or complex numbers. In certain aspects, the occupancy-centric algorithm 250 may include signal processing techniques and algorithms used for computer vision and image processing tasks. The first radio device 110 may store some, none, or all of the received CSI and/or may compare some, none, or all of the received CSI to previously received CSI (stored CSI). The first radio device 110 may compare received CSI from each packet to stored CSI for one packet and/or multiple packets and/or averages and/or running averages and/or sliding window averages of stored CSI. The stored CSI may include amplitude and phase and timing information for each subcarrier of a radio signal or the stored CSI may be some subset of amplitude and phase and timing information on any or all of the subcarriers of the received radio signal.

The first radio device 110 may store multiple CSIs and may store multiple copies of CSI. The multiple stored CSIs may include, but are not limited to, CSIs from previous time periods, from a third or other radio devices, from a known time when a space 105 was unoccupied, versions that have been processed differently such as having the noise removed, having been filtered differently, having different numbers of averages or different length averaging windows, versions that have been input by a user or another program, versions that have been calculated using a different algorithm, and the like. In embodiments, the first radio device 110 may maintain a running average of previously received CSIs and may compare newly received CSIs to the running average. If a certain value calculated from the CSIs deviates in a newly received CSI from that calculated for the running average CSI, then the first radio device 110 may interpret that deviation as a change in the radio environment consistent with human occupancy.

The first radio device 110 may quantify deviations between recent and older CSIs and may provide different output signals based on how much the compared CSIs deviate. For example, the first radio device 110 may compute the amplitude of some of the received subcarriers and associate that number with an energy of the received signal. The first radio device 110 may average some number of received packets to obtain an average energy of received packets. The first radio device 110 may continue to update this average by calculating it from the previous 2 CSIs, 5 CSI's, 10 CSIs, 100 CSIs, 1000 CSIs, 10,000 CSIs, 100,000 CSIs, 1,000,000 CSIs, or any other number of CSIs. The number of CSIs in a running average may be a settable parameter and that parameter may be set by a user, a controller, an algorithm, or otherwise. In some aspects, the number of CSIs in a running average may be variable and may be changed to adjust system performance.

If the energy of a received signal deviates from the average energy by 0.0001%, by 0.001%, by 0.01%, by 0.1%, by 1%, by 10%, by 100%, or any other amount, the first radio device 110 may associate that deviation with the presence of a human in the radio environment. One skilled in the art will understand that although the deviations listed above are given in percentages, that there are many ways to quantify deviations and that any of these types of quantifiers are within the scope of the disclosure. For example, any type of value, number, ratio, percentage and the like may be used to set a threshold value and/or range for a system indicator.

In certain implementations, a first radio device 110 may not associate a deviation in CSI with human occupancy unless the deviation has a certain value and/or has been measured for some number of packets and/or some amount of time and/or with some frequency, and the like. The deviation level and/or the number of packets with CSI of particular values and/or the amount of time that packets arrive with certain CSI levels and/or the frequency with which packets with certain levels arrive may be settable parameters, which can be by a user, a controller, an algorithm, and the like.

According to various aspects of the present disclosure, a first radio device 110 may receive packets from a second radio device 100 for some period of time before it compares newly received CSI to previous or stored CSI. A first radio device 110 may receive a certain number of packets and/or may receive packets for a certain amount of time, where the number of packets and/or amount of time may be settable parameters. The first radio device 110 may analyze the received CSI and may begin to calculate average CSI values. These average CSI values may be background CSI levels and may be associated with the state of the environment (space 105) at certain times during operation of the sensor system 100. For example only, a first radio device 110 may receive packets and calculate an average CSI when there is little or no movement in the space 105, and this CSI may be compared to CSI received later to look for deviations in the data that might indicate the presence of one or more humans. The sensor system 105 may be programmed to collect background CSI when the system starts up and/or at certain times of day, days of the week, times of the month and the like when the space 105 is known to be or is likely unoccupied. In embodiments, multiple background CSI may be stored and used for comparing to newly arriving CSI. In embodiments, multiple background CSI may be accessed from a marketplace of data having relevant data sets allowing for comparison to newly arriving CSI. In embodiments, different background CSI may be compared to each other and the sensor system 100 may monitor and/or report differences and/or trends in background CSI.

The sensor system 100 may continuously generate an output signal (such as occupancy signal at 350 and/or control signal(s) at 360) or it may generate an output signal in response to a request or it may initiate the generation of an output signal based on sensor data. If continuously generating an output signal, the level of that signal and/or the data in that signal may change to indicate that a change in the occupancy of the space 105. For example only, the sensor system 100 may generate an output signal every time a received CSI deviates from a stored CSI by a specified amount. Alternatively, the output signal may only be generated if some number of CSIs have deviated by a specified amount, or if some CSIs have deviated by a specified amount over some period of time, or if some CSIs have deviated and some other signal, threshold, input, etc. has a specified value. It should be appreciated that the output of the sensor system 100 may be based on multiple sensor inputs, environmental conditions, system settings, and other factors described herein.

As mentioned herein, the sensor system 100 may send an output signal to a controller to control a system that operates in the radio environment (space 105) of the sensor system 100. A radio device 110 in the sensor system 100 may include the controller or, alternatively, the controller may be separate from the radio device 110 and the output signal may be delivered to the controller via a circuit trace, a wire, an optical fiber, a wireless signal, an optical signal or any combination of known transmission protocols and media. In some aspects, the output signal from the sensor system 100 may be part of a feedback loop that is used to control a system in the space 105. For example only, the output signal may be part of a feedback loop to control any, some, or all of heating, cooling, ventilation, security, lighting, power, and entertainment systems. Additionally, the output signal may be part of an open loop control circuit or system to control any, some, or all of heating, cooling, ventilation, security, lighting, power, and entertainment systems.

While this disclosure has described a sensor system 100 inside or outside a building, the sensor system 100 can be applied to other types of scenarios and other space(s) 105. For example only, the disclosed sensor systems 100 could be used to detect the presence of humans in disaster scenarios such as collapsed buildings, caves, mines and the like. In such scenarios, the sensor systems 100 could be used to determine if and how many humans are breathing and at what rate their hearts are beating. Likewise, the sensor systems 100 could be used to determine if and how many humans might be hidden in an enclosure during a hostage or kidnapping situation and may determine if and how many humans are enclosed in a container such as a shipping crate, a trucking crate, below deck on a boat, and the like. In addition to human presence, the sensor systems 100 could be used to monitor the health of humans and/or animals in an area. For example only, this disclosure could generate an output signal that is related to the breathing rate and or heartrate of any living beings within a space 105. Such sensor systems 100 could be used to monitor the breathing of babies and protect against sudden infant death syndrome. Such systems could also monitor the sleeping of people with sleep apnea and sound an alarm or adjust a bed or environmental setting if a person's breathing becomes too erratic or stops.

Sensor Systems in Value Chain Network

The sensor system 100 may be used with a value chain network such as a logistics value chain network. The logistics value chain network or infrastructure may include warehouses, distribution centers, ships, trucks, aircraft, order and information systems, workers, cargo airports, container ports, oceans, geographic features, railway lines, highways, streets, customer homes, workplaces, etc. Parties involved may be suppliers, customers, and partners that may be typically involved in logistics and shipping. The logistics value chain network may relate to various workflows that may be used in shipping, maritime, port/border crossing, logistics, fulfillment centers, reverse logistics, packing, picking, assembly, delivery, installation, etc.

In typical examples, the value chain network such as the logistics value chain network or supply chain may involve ordering of products which are fulfilled by manufacturers through a supply chain where suppliers in various supply environments, operating production facilities or resellers or distributors for others, make a product available at a point of origin in response to an order. The product may be passed through the supply chain, being conveyed and stored via various hauling facilities and distribution facilities, such as warehouses, fulfillment centers, and delivery systems, such as trucks, trains, and other vehicles. In many cases, maritime facilities and related infrastructure, such as ships, barges, docks and ports may be used to transport products over waterways between the points of origin and one or more destinations. The related infrastructure (including e.g., warehouses, facilities, vehicles, etc.) may be monitored by the sensor system 100.

Value chain network entities may be involved in a wide range of value chain activities such as supply chain activities, logistics activities, demand management and planning activities, delivery activities, shipping activities, warehousing activities, distribution and fulfillment activities, inventory aggregation, storage and management activities, marketing activities, and many others, as involved in various value chain network processes, workflows, activities, events and applications. The sensor system 100 may determine value chain recommendations based on monitoring of at least occupancy data related to these activities in spaces.

Object classes for each type of value chain network entity may include product, infrastructure, workers, operators, owners, enterprises, suppliers, distributors, logistics providers, customers, resellers, etc. The applications may involve any of the wide variety of assets, systems, devices, machines, components, equipment, facilities, individuals or other entities mentioned throughout this disclosure.

The sensor system 100 may be used with value chain processes such as shipping processes, hauling processes, maritime processes, inspection processes, hauling processes, loading/unloading processes, packing/unpacking processes, configuration processes, assembly processes, installation processes, quality control processes, environmental control processes (e.g., temperature control, humidity control, pressure control, vibration control, and others), border control processes, port-related processes, software processes (including applications, programs, services, and others), packing and loading processes, financial processes (e.g., insurance processes, reporting processes, transactional processes, and many others), testing and diagnostic processes, security processes, safety processes, reporting processes, asset tracking processes, and many others.

Examples of Value Chain Network Entities

In examples, value chain network entities may include, for example, products, suppliers, producers, manufacturers, retailers, businesses, owners, operators, operating facilities, customers, consumers, workers, mobile devices, wearable devices, distributors, resellers, supply chain infrastructure facilities, supply chain processes, logistics processes, reverse logistics processes, demand prediction processes, demand management processes, demand aggregation processes, machines, ships, barges, warehouses, maritime ports, airports, airways, waterways, roadways, railways, bridges, tunnels, online retailers, ecommerce sites, demand factors, supply factors, delivery systems, floating assets, points of origin, points of destination, points of storage, points of use, networks, information technology systems, software platforms, distribution centers, fulfillment centers, containers, container handling facilities, customs, export control, border control, drones, robots, autonomous vehicles, hauling facilities, drones/robots/AVs, waterways, port infrastructure facilities, or many others In other examples, a set of value chain network entities may include, without limitation: a policy management application such as for deploying one or more policies, rules, or the like for governance of one or more value chain network entities or applications, such as to govern execution of one or more workflows (which may involve configuring polices in the platform on a per-workflow basis), to govern compliance with regulations (including maritime, food & drug, medical, environmental, health, safety, tax, financial reporting, commercial, and other regulations as described throughout this disclosure or as would be understood in the art), to govern provisioning of resources (such as connectivity, computing, human, energy, and other resources), to govern compliance with corporate policies, to govern compliance with contracts (including smart contracts, wherein the platform may automatically deploy governance features to relevant entities and applications, such as via connectivity facilities), to govern interactions with other entities (such as involving policies for sharing of information and access to resources), to govern data access (including privacy data, operational data, status data, and many other data types), to govern security access to infrastructure, products, equipment, locations, or the like, and many others.

Examples of Workers, Suppliers, and Customers in Value Chain Network

Workers may include delivery workers, shipping workers, barge workers, port workers, dock workers, train workers, ship workers, distribution of fulfillment center workers, warehouse workers, vehicle drivers, business managers, engineers, floor managers, demand managers, marketing managers, inventory managers, supply chain managers, cargo handling workers, inspectors, delivery personnel, environmental control managers, financial asset managers, process supervisors and workers (for any of the processes mentioned herein), security personnel, safety personnel and many others). Suppliers may include suppliers of goods and related services of all types, component suppliers, ingredient suppliers, materials suppliers, manufacturers, and many others. Customers may include consumers, licensees, businesses, enterprises, value added and other resellers, retailers, end users, distributors, and others who may purchase, license, or otherwise use a category of goods and/or related services.

Examples of Spaces in Value Chain Network

Within the value chain network (e.g., logistics value chain network), the sensor system 100 may analyze channel responses, as described above, to determine information about a value chain space (e.g., space 105). The space 105 may be within ships, trucks, aircraft, barges, warehouses, ports, distribution centers, containers, container handling facilities, cargo airports, container ports, customer homes, workplaces, etc. As described above, the channel responses may be channel impulse responses (CIR), channel frequency responses (CFR), channel state information (CSI), received signal strength indications (RSSI), or any other type of channel response. Information about the value chain space may include, e.g., whether something was moving in the space 105, whether something was breathing and how fast it was breathing in the space 105, and/or whether something with a heartbeat and the rate of the heartbeat was in the space 105. In some examples, as described above, signaling protocols may be used (e.g., WiFi protocols) such that channel information may be generated which may be referred to as CSI.

In some examples, the spaces may be part of a wide range of operating facilities in the value chain network such as loading and unloading docks, storage and warehousing facilities, vaults, distribution facilities and fulfillment centers, air travel facilities (including aircraft, airports, hangars, runways, refueling depots, and the like), maritime facilities (such as port infrastructure facilities (such as docks, yards, cranes, roll-on/roll-off facilities, ramps, containers, container handling systems, waterways, locks, and many others), shipyard facilities, floating assets (such as ships, barges, boats and others), facilities and other items at points of origin and/or points of destination, hauling facilities (such as container ships, barges, and other floating assets, as well as land-based vehicles and other delivery systems used for conveying goods, such as trucks, trains, and the like).

Occupancy-Centric Algorithm for Value Chain Network

The sensor system 100 may use an occupancy-centric algorithm (e.g., occupancy-centric algorithm 250), as described above, to determine human occupancy in the value chain space (e.g., space 105). The sensor system may further determine a value chain recommendation based on the determined occupancy in the value chain space. For occupancy sensing applications, the occupancy-centric algorithm may be used in occupant processing, occupancy-centric processing, occupancy-finding processing or similar, which may be performed based on the occupancy-centric algorithm or other occupant algorithms, occupancy-centric algorithms, or similarly named algorithms. As described above, in some examples, the sensor system 100 may recognize and monitor individuals as unique humans from one another due to their radio signature. For example, certain humans may impact the amplitude and/or phase and/or timing of the radio signals in a way that is recognizable to the occupancy-centric algorithms running in the sensor system 100. Tracking people individually may include detecting one worker from another worker in the value chain space each day, week, etc. This information may be used for determining efficiency of each individual worker and/or whether the individual worker may be a distraction to other workers and/or whether the worker may be a bottleneck and require training, etc.

Evolution of Occupancy-Centric Algorithm for Value Chain Network

The occupancy-centric algorithm 250 may change and evolve over time with respect to the value chain network (e.g., logistics value chain network). As described above, the occupancy-centric algorithm 250 may be altered using training algorithms, learning algorithms, machine learning algorithms, artificial intelligence algorithms, and the like. In some examples, the occupancy-centric algorithm 250 may include portions of what might be considered learning algorithms, training algorithms, machine learning algorithms, and/or artificial intelligence algorithms. Shallow learning algorithms, deep learning algorithms, deep neural networks, and the like may be utilized to improve performance of the sensor system 100 and/or occupancy-centric algorithm 250 with respect to the value chain network. The occupancy-centric algorithm 250 may change and evolve over time, either automatically or in response to some sort of external input(s) from spaces of the value network. The sensor system 100 may determine new value chain recommendations based on the evolution of the occupancy-centric algorithm.

Monitor and Control of Environment Systems of Value Chain Space

Internet of Things (IoT) systems and devices of the value chain network may be used with the sensor system 100. For example, IoT systems and devices may include thermostats, lighting systems, and speakers that may be enabled with onboard network connectivity and processing capability, often including a voice controlled intelligent agent that allows device control and triggering of certain application features, such as playing music, or even changing temperature. As artificial intelligence capabilities increase, more and more computing and networking power may be moved to network-enabled edge IoT devices and systems that reside in value chain networks (e.g., supply environments) and in all of the locations, systems, and facilities that populate the path of a product within the infrastructure of the value chain network (e.g., logistics value chain network) e.g. from a loading dock of a manufacturer to the point of destination of a customer. The need and opportunity exist for dramatically improved intelligence, control, and automation of all of the factors (e.g., based on systems and devices) involved in the value chain network. The sensor system 100 may include environmental control processes (e.g., temperature control, humidity control, pressure control, vibration control, and others). For example, the sensor system 100 may include and/or engage temperature monitoring systems, heat flow monitoring systems, biological measurement systems, chemical measurement systems, ultrasonic monitoring systems, radiography systems, etc.

In examples, a variety of gestures from the workers may be detected by the sensor system 100. These detected gestures may be used to initiate steps that could be taken to control, adjust, and/or vary heating, cooling, ventilation, security, lighting, power, entertainment systems, and other systems in or associated with the value chain space (e.g., space 105). For example, a worker wipes sweat on forehead indicating that the worker may be hot, or worker puts on jacket indicating that the worker may be cold. Besides gestures, the sensor system 100 may be able to detect sweat indicating too hot or movement of hair or goose bumps indicating too cold and/or temperature of person's skin may be additionally measured. The worker may use other gestures (e.g., pointing to ear) indicating that worker cannot hear which means that space is too noisy such that devices may be controlled to remove noise (e.g., fan of ventilation system may be turned down in terms of power) or volume of devices may need to be increased.

Output signals may include a temperature setting or a range of temperature settings that a heating/cooling system (e.g., increasing temperature with a heater and decreasing temperature with AC) should attain in the space 105. This output signal may be a signal that is suitable for input into another data analysis stage, processing stage, signal extraction stage, signal determination stage, or similar control or analysis system to adjust the temperature accordingly. Such heating systems may receive occupancy and/or control signals from the sensor system 100 and may increase, decrease, or maintain the amount of heat supplied to the space 105. Similarly, cooling systems may receive occupancy and/or control signals from the sensor system 100 and may increase, decrease, or maintain the amount of cooling supplied to the space 105.

Other environment experiences that may be adjusted include humidity, airflow, etc. The sensor system 100 may provide occupancy and/or control signals to heating systems (using heater), cooling systems (using AC), ventilation systems (e.g., increase speed of fans and/or activate more fans or activate fans in particular section of space) to decrease humidity and/or increase airflow and/or maintain humidity and airflow when needed. The ventilation systems (e.g., fans) may receive the occupancy and/or control signals from the sensor system 100 and may increase, decrease, or maintain the amount of ventilation supplied to the space 105. Ventilation may be adjusted based on noise. For example, if there are enough people in room trying to talk to one another and gestures from workers indicate that they are having difficulty hearing which appears to be due to noise from fans, then ventilation system may adjust airflow accordingly. For example, motor speed may be lowered for fans closer to workers (which may decrease noise) or may be deactivated while motor speed may be increased for fans further away from workers. The fans further from workers may have less noise impact due to distance. This allows for airflow to be maintained while minimizing noise in particular area of space 105 based on monitoring of occupancy information of workers in the particular area.

In some examples, as described above, heating, cooling and/or ventilation systems may be automatically adjusted (e.g., using thermostats) in the value chain space (e.g., space 105) based on whether or not workers are present. For example, if a worker is present, the thermostat may adjust the heating, cooling and/or ventilation levels to the levels comfortable for human occupied spaces. The levels determined to be comfortable for human occupied spaces may be occupancy-specific, room-specific, area-specific, building-specific, time-specific, outdoor temperature specific, season-specific, location-specific, energy-price specific, energy source specific and the like based on workflows within the value chain space (e.g., space 105). If the data analysis determines that an occupant such as a worker is not present, heating, cooling and/or ventilation levels may be set to levels that conserve energy (setback temperature and ventilation settings). If there are no workers in the value chain space, then energy may be conserved by cutting off ventilation and/or heating and/or cooling systems. Also, when there no workers in the value chain space, heating, cooling and/or ventilation levels may be set to levels that still properly maintain products (e.g., dependent on products being stored) that may be stored in value chain space or a particular area of the value chain space e.g. so that products are not damaged from excessive heat or humidity.

Other systems such as security systems, lighting systems, power systems, entertainment systems, kitchen systems (e.g., coffee maker devices or expresso machines), speaker or intercom systems, and other systems or devices associated with the value chain space (e.g., space 105) may also be monitored and controlled by the sensor system 100. The control and monitoring may be based on occupancy of workers in vicinity of devices and usage of devices related to these systems. For example, if no workers are in the space 105 then devices of these systems may be deactivated or turned off (e.g., no lighting since no workers) to conserve energy. Lighting may be adjusted depending on number of workers in particular section of the space 105 such that lighting may need to be increased when more people enter the particular section. Lighting may need to be adjusted depending on sunlight from windows (e.g., due to time of day such as night vs. daytime light or weather such as sunny weather vs. cloudy rainy weather) such that lighting may be decreased when sunny and increased when cloudy or night. Volume of entertainment systems may be adjusted automatically based on noise in space 105. For example, entertainment systems may receive occupancy and/or control signals from the sensor system 100 and may increase, decrease or maintain the volume, channel, settings and the like of any audio, video and/or other entertainment signals supplied. Similarly, volume of speaker or intercom systems may be increased or decreased based on noise in space and/or gestures from workers indicating difficulty hearing. Power systems may be monitored based on usage to optimize power usage while minimizing power waster where power is not needed. Kitchen systems may be monitored for usage and occupancy nearby the kitchen systems such that when no workers are nearby, the kitchen systems may be either inactivated or switched to a low power state. Also, the sensor system 100 may detect overly high usage some kitchen systems such that the sensor system 100 determines a value chain recommendation including adding kitchen devices such as coffee makers where there is a need based on occupancy data and usage data. Security systems may be monitored for whether security devices should be activated (e.g., sprinklers for fire) and/or other security actions be made (e.g., call emergency personnel) based on data of environmental experiences detected by the sensor system 100. The sensor system 100 may monitor and control security systems, lighting systems, power systems, entertainment systems, kitchen systems, speaker or intercom systems, and other systems or devices associated with the value chain space based on other factors and/or characteristics of environmental experiences detected by the sensor system 100.

The sensor system 100 may adjust these systems and/or have specific settings to use during a pandemic. For example, the sensor system 100 may direct ventilation more frequently when workers are together in the same space. Further, ventilation may be activated such that fans in spaces are specifically activated when groups of workers are within a distance (e.g., vicinity) of fans. Alarms may occur when occupancy data indicates that workers are not social distancing (e.g., not six feet from one another) and/or do not appear to be wearing masks. Alarms may be used to indicate ventilation filters needing replacement well before the filters are no longer effective.

Security System of Value Chain Space for Disaster Service

In some examples, the sensor system 100 may be used to detect the presence of workers in disaster scenarios for the value chain space. Disaster scenarios may include collapsed buildings, caves, or mines, ship or train or vehicle accidents, fires in buildings, criminal activity, worker injuries from work-related accidents, and the like. The sensor system 100 may then automatically trigger the security system based on these detected disasters to provide the appropriate response based on the disaster. For example, in case of a fire in a warehouse, the sensor system 100 may direct the security system to trigger emergency devices such as fire alarms and/or fire sprinklers (e.g., if they haven't already been triggered) and then automatically contact emergency personnel with information about disaster and status of warehouse and health of workers.

The sensor system 100 may also include an incident management application such as for managing events, accidents, and other incidents that may occur in one or more environments involving value chain network entities, such as, without limitation, vehicle accidents, worker injuries, shutdown incidents, property damage incidents, product damage incidents, product liability incidents, regulatory non-compliance incidents, health and/or safety incidents, traffic congestion and/or delay incidents (including network traffic, data traffic, vehicle traffic, maritime traffic, human worker traffic, and others, as well as combinations among them), product failure incidents, system failure incidents, system performance incidents, fraud incidents, misuse incidents, unauthorized use incidents, and many others).

Disruptions in Value Chain Network

To prevent disruptions, the sensor system 100 may detect information useful to a value chain network (e.g., a logistics value chain network) for preventing disruptions. For example, occupancy signals may indicate that a certain number of workers are present over a predetermined threshold causing impact to workflow, that an animal is present, that a window has opened, that a door has opened, that at least one person is present but not moving, that a person has fallen, that a person has moved to a different space 105, or any other condition of the space 105 that may impact the logistics value chain network. The sensor system 100 may determine a value chain recommendation based on these disruptions. The sensor system 100 may determine that these conditions are disruptions based on a combination of workflow results and/or occupancy information indicating disruption to workflow operations such that an action may be suggested to either eliminate or at least minimize the disruption. For example, it may be determined that when a particular door is opened as often as it is on some days, this action may be impacting worker productivity in the vicinity such that recommendation may be to use a different door or use the particular door at specific times of day thereby eliminating or at least minimizing this disruption.

Monitor Current Occupancy Against Standard Occupancy for Value Chain Network

The sensor system 100 may compare occupancy of different spaces along the value chain network to standard occupancy to prevent maxing out acceptable capacity for these spaces. The sensor system 100 may then determine whether the current occupancy is higher or lower compared to standard occupancy for space to maintain safety for workers and prevent accidents. The standard occupancy may be an industry max number of workers that can safely work in space (e.g., capacity limits) while complying with any government rule and/or regulations (e.g., prevent fire hazard conditions). The standard occupancy may also be based on providing workers with reasonable space to interact but also do their job efficiently based on industry standard. This max may vary for space to space or room to room such that an elevator space may have a more limited standard occupancy compared to standard occupancy of a warehouse space. The sensor system 100 may determine a value chain recommendation based on occupancy data such that warnings may be provided when detected occupancy is above standard occupancy in spaces during any period of time.

Operating Recommendations for Value Chain Network

The sensor system 100 may receive data including information related to various operating parameters of the value chain network over a particular historical time period (e.g., hours, days, week, 12 months). This data may also provide information on the typical values of various operating parameters under normal conditions. Some examples of operating parameters may include product demand, procurement lead time, productivity, inventory level at one or more warehouses, inventory turnover rates, warehousing costs, average time to transport product from warehouse to shipping terminals, overall cost of product delivery, service levels, etc. The sensor system 100 may use this data to provide operating recommendations where needed to compensate for changes in operating parameters, which can be shown to improve operation and performance of the value chain network. In some examples, simulation models of the value chain network may be created based on the data. The simulation models may help in visualizing the value chain network as a whole and in predicting how changes in operating parameters affect the operation and performance of the value chain network. In examples, the simulation model may be a sum of multiple models of different subsystems of the value chain network.

Monitoring Physical Activities of Workers in Value Chain Network

The sensor system 100 may include a physical process observation system such as for tracking physical activities of workers that may be used for determining value chain recommendations. Physical activities of workers (e.g., shippers, delivery workers, packers, pickers, assembly personnel, customers, merchants, vendors, distributors and others), physical interactions of workers with other workers, interactions of workers with physical entities like machines and equipment, and interactions of physical entities with other physical entities, including, without limitation, by use of video and still image cameras, motion sensing systems (such as including optical sensors, LIDAR, IR and other sensor sets), robotic motion tracking systems (such as tracking movements of systems attached to a human or a physical entity) and many others. Machine state monitoring systems may include onboard monitors and external monitors of conditions, states, operating parameters, or other measures of the condition of any value chain entity, such as a machine or component thereof, such as a machine, such as a client, a server, a cloud resource, a control system, a display screen, a sensor, a camera, a vehicle, a robot, or other machine. Sensors and cameras and other IoT data collection systems (including onboard sensors, sensors or other data collectors (including click tracking sensors) in or about a value chain environment (such as, without limitation, a point of origin, a loading or unloading dock, a vehicle or floating asset used to convey goods, a container, a port, a distribution center, a storage facility, a warehouse, a delivery vehicle, and a point of destination), cameras for monitoring an entire environment, dedicated cameras for a particular machine, process, worker, or the like, wearable cameras, portable cameras, cameras disposed on mobile robots, cameras of portable devices like smart phones and tablets, and many others.

The sensor system 100 may interact with value chain network entities based on worker data such as locations of workers (including routes taken through a location, where workers of a given type are located during a given set of events, processes or the like, how workers manipulate pieces of equipment, cargo, containers, packages, products or other items using various tools, equipment, and physical interfaces, the timing of worker responses with respect to various events such as responses to alerts and warnings), procedures by which workers undertake scheduled deliveries, movements, maintenance, updates, repairs and service processes; procedures by which workers tune or adjust items involved in workflows, and many others. The sensor system may include a physical process observation that may include tracking positions, angles, forces, velocities, acceleration, pressures, torque, and the like of a worker as the worker operates on hardware, such as on a container or package, or on a piece of equipment involved in handling products, with a tool. Such observations may be obtained by any combination of video data, data detected within a machine (such as of positions of elements of the machine detected and reported by position detectors), data collected by a wearable device (such as an exoskeleton that contains position detectors, force detectors, torque detectors and the like that is configured to detect the physical characteristics of interactions of a human worker with a hardware item for purposes of developing a training data set). The sensor system 100 may use this physical activities data and worker data (e.g., physical process interaction observations) for determining value chain recommendations (e.g., training suggested where needed) in order to improve value chain workflows.

Productivity Recommendations Based on Efficiency for Value Chain Network

The sensor system 100 may determine a value chain recommendation including productivity recommendations based on efficiency-related information. Productivity may be based on occupancy numbers hourly, daily, weekly, etc. based on the sensor system 100 monitoring workers during these time periods for output and efficiency. Further, the sensor system 100 may use RFID and asset tracking systems for tracking goods as they move through spaces of a supply chain and use occupancy data over time and routing systems to improve an efficiency of route selection within spaces and between locations (e.g., improve transportation route between distribution buildings).

There is an increasing pressure to improve value chain performance and productivity (e.g., supply chain performance). Specifically, customer expectations for speed of delivery have placed increased pressure on supply chain efficiency and optimization. Accordingly, the sensor system 100 may determine value chain recommendations aimed at improving supply chain productivity. Specifically, these recommendations may be directed towards improving speed and personalization with respect to customer expectations. Specifically, for example, recommendations may provide unified orchestration of supply and demand. In some cases, the recommendation may suggest training be provided if resulting output (e.g., productivity) may not be sufficient based on number of workers located in space. For example, productivity of one space of interest may be compared to productivity of another space or a standard productivity. The sensor system 100 may determine that the number of workers may be sufficient for the associated workflow and the space of interest should have higher productivity based on comparison. Accordingly, training may be suggested and/or workflow of space of interest may be further investigated automatically for bottle necks and/or disruptions that may be impacting productivity. For example, as part of the investigation, sensor system 100 may monitor speed of workers in space which may be compared to workers in other spaces part of the same workflow or standard workers part of the same workflow.

Reallocation of Worker Resources in Value Chain Network

The sensor system 100 may reallocate human assets such as worker resources based on human worker traffic and productivity of workflows. Reallocation of human resources may be needed based on occupation data such that if there are spaces that need more assistance from workers and other spaces where there are workers that do not have enough work (i.e., additional bandwidth or too many workers) then reallocation may be suggested when determining value chain recommendations. The workers with not enough work may be moved to spaces where assistance is needed based on the value chain recommendations. In other examples, training may be needed for workers where productivity is a result of lack of training where number of workers is reasonable for workflow. In general, the value chain recommendations may be determined with a goal of matching one or more demand factors with one or more supply factors in order to match needs and capabilities of value chain network entities.

Remove or Limit Worker Redundancies in Value Chain Network

The sensor system 100 may provide automated coordination and unified orchestration of supply and demand to remove or limit worker redundancies in the value chain network. For example, the sensor system 100 may use artificial intelligence-type systems (e.g., machine learning, expert systems, self-organizing systems, and the like including such systems) for coordinating supply chain activities. Use of artificial intelligence may further enrich the emerging nature of self-adapting systems, including Internet of Things (IoT) devices and intelligent products and the like that not only provide greater capabilities to end users, but can play a critical role in automated coordination of supply chain activities. This may be used to remove or at least limit redundancies where there is too much overlap between workers doing the same tasks of one or more workflows. For example, where a workflow typically requires 6-8 workers max but currently 15 workers are involved in tasks this same workflow, the sensor system 100 may determine a value chain recommendation suggesting at least 7 of the workers should be removed from workflow and these workers be moved to other workflows (i.e., reallocate worker resources).

Monitor Health of Workers in Value Chain Network

The sensor system 100 may be used to track and monitor health of workers in value chain network (e.g., logistics value chain network). For example, the sensor system 100 may use a biological measurement system to monitor health of worker in a value chain space. The sensor system 100 may receive health information about the workers. This health information may be useful for anticipating hazardous situations and/or preventing spread of diseases or medical disasters from occurring. The sensor system 100 may have access to real time dynamic data captured by IoT devices and sensors on in nearby workers to monitor and track health data of the workers. These devices and sensors may be supported with natural language capabilities enabling them to interact with workers and answer any questions about the health of each worker. The sensor system 100 may use this health data to determine and provide value chain recommendations that may specific to each worker, which can be shown to anticipate health conditions in workers based on health data received. The sensor system 100 may be configured to follow regulatory policies (e.g., privacy policies such as HIPAA) as required when monitoring health of workers and providing recommendations.

The sensor system 100 may include a self-organizing neural network that organizes structures or patterns in the data, such that they can be recognized, analyzed, and labeled, such as identifying structures as corresponding to individuals, disease conditions, health states, activity states, and the like. Such a network may be used to model or exhibit dynamic temporal behavior, such as involved in dynamic systems, such as a wide variety of the disease conditions, health states, and biological systems, such as a body experiencing multiple different diseases or health conditions, or the like, where dynamic system behavior involves complex interactions that an observer may desire to understand, diagnose, predict, control, treat and/or optimize. For example, the recurrent neural network may be used to anticipate the state (such as a maintenance state, a health state, a disease state, or the like), of a worker, such as one interacting with a system, performing an action, or the like. The sensor system 100 may use this anticipated state information to determine and provide value chain recommendations to workers.

The sensor system 100 may monitor for semi-sentient problem recognition which involves more than mere linkages of data and operational states of entities engaged in a value chain. Problem recognition may also be based on human factors, such as perceived stress of production supervisors, shippers, and the like. Human factors for use in semi-sentient problem recognition may be collected from sensors that facilitate detection of human stress level and the like (e.g., wearable physiological sensors, and the like). The sensor system 100 may use this semi-sentient information to determine and provide value chain recommendations to workers.

Sensor System Using Digital Twins for Value Chain Network

In some examples, the sensor system 100 may use a digital twin corresponding to the value chain network. The sensor system 100 may be configured to learn on a training set of outcomes, parameters, and data collected from data sources in the value chain network and data received by the sensor system 100 (e.g., occupancy data) to train an artificial intelligence/machine learning system to use information from a set of digital twins. The digital twins may represent entities of the value chain network to estimate costs and actions required for a particular course of action in the value chain network.

In an example, the sensor system 100 may include warehousing twins (also referred to as warehouse digital twins). The warehousing twins may combine a 3D model of the warehouse with inventory and operational data including size, quantity, location, and demand characteristics of different products. The warehousing twins may be used to collect sensor data of a connected warehouse, as well as data on the movement of inventory and personnel within the warehouse. Warehousing twins may assist in optimizing space utilization and aid in identification and elimination of waste in warehouse operations. The simulation using warehousing twins of the movement of products, workers, and material handling equipment may enable warehouse managers to test and evaluate the potential impact of layout changes or the introduction of new equipment and new processes. The sensor system 100 may use this information from digital twins (e.g., warehousing twins or warehouse digital twins) to determine and provide value chain recommendations that improve value chain workflows.

Warehousing Twins—Reallocation of Resources

The sensor system 100 may include an example warehouse digital twin kit system having a warehousing twins that may provide information on reallocation of resources. The warehousing twins may be in a virtual space representing models of warehouses in the real space. In some examples, the warehousing twins may provide a portfolio overview of warehouse entities in the form of a 3D information map containing all the warehouse entities. A specific entity on the map may be selected providing information about inventory, operational and health data from the warehousing twin. The warehouse digital twin kit system may consolidate information from multiple warehousing twins and may provide a holistic view. The consolidated view may assist in optimizing operations across warehouse entities by adjusting stock locations and worker levels to match current or forecasted demand. Display of the information from the warehouse digital twin kit system may be provided. In some examples, monitoring of occupancy may be provided with respect to maximizing resources. As described above, worker resources may be reallocated where workers are maxed out (e.g., beyond a threshold in terms of filling need) in one space whereas another space may need worker resources. The sensor system 100 may use this information from digital twins (e.g., warehousing twins or warehouse digital twins) to determine and provide value chain recommendations that suggest worker resources be reallocated from the maxed-out space to the space needing help/assistance.

Digital Twins—Evolving from Training

The sensor system 100 may include analytics that are obtained from digital twins of the value chain network entities and their interactions with one another provide a systemic view of the value chain network as well as its systems, sub-systems, processes and sub-processes that may evolve from training. This may help in generating new insights into ways the various systems and processes may be evolved to improve their performance and efficiency. In examples, the sensor system 100 may include a platform and applications that generate and update a self-expanding digital twin that represents a set of value chain entities. The self-expanding digital twin may continuously keep learning and expanding in scope as more and more data may be collected thus more scenarios may be encountered. As a result, the self-expanding twin may evolve with time and take on more complex tasks and answer more complex questions posed by a user of the self-expanding digital twin. The sensor system 100 may use this evolution to simultaneously adjust or evolve the occupancy-centric algorithm. The sensor system 100 may use this evolution information to determine and provide value chain recommendations according to insights.

The sensor system 100 may provide training in optimization, such as training a neural network to optimize one or more systems based on one or more optimization approaches. These approaches may include Bayesian approaches, parametric Bayes classifier approaches, k-nearest-neighbor classifier approaches, iterative approaches, interpolation approaches, Pareto optimization approaches, algorithmic approaches, and the like. Feedback may be provided in a process of variation and selection, such as with a genetic algorithm that evolves one or more solutions based on feedback through a series of rounds. The sensor system 100 may use this optimization to adjust or evolve the occupancy-centric algorithm based on the genetic algorithm. The sensor system 100 may use this optimization information to determine and provide value chain recommendations according to optimization information from the neural network.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known procedures, well-known device structures, and well-known technologies are not described in detail.

While only a few embodiments of the present disclosure have been shown and described, it will be obvious to those skilled in the art that many changes and modifications may be made thereunto without departing from the spirit and scope of the present disclosure as described in the following claims. All patent applications and patents, both foreign and domestic, and all other publications referenced herein are incorporated herein in their entireties to the full extent permitted by law.

The methods and systems described herein may be deployed in part or in whole through a machine that executes computer software, program codes, and/or instructions on a processor. The present disclosure may be implemented as a method on the machine, as a system or apparatus as part of or in relation to the machine, or as a computer program product embodied in a computer readable medium executing on one or more of the machines. In embodiments, the processor may be part of a server, cloud server, client, network infrastructure, mobile computing platform, stationary computing platform, or other computing platforms. A processor may be any kind of computational or processing device capable of executing program instructions, codes, binary instructions and the like, including a central processing unit (CPU), a general processing unit (GPU), a logic board, a chip (e.g., a graphics chip, a video processing chip, a data compression chip, or the like), a chipset, a controller, a system-on-chip (e.g., an RF system on chip, an AI system on chip, a video processing system on chip, or others), an integrated circuit, an application specific integrated circuit (ASIC), a field programmable gate array (FPGA), an approximate computing processor, a quantum computing processor, a parallel computing processor, a neural network processor, or other types of processor. The processor may be or may include a signal processor, digital processor, data processor, embedded processor, microprocessor or any variant such as a co-processor (math co-processor, graphic co-processor, communication co-processor, video co-processor, AI co-processor, and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more threads. The thread may spawn other threads that may have assigned priorities associated with them; the processor may execute these threads based on priority or any other order based on instructions provided in the program code. The processor, or any machine utilizing one, may include non-transitory memory that stores methods, codes, instructions and programs as described herein and elsewhere. The processor may access a non-transitory storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache, network-attached storage, server-based storage, and the like.

A processor may include one or more cores that may enhance speed and performance of a multiprocessor. In embodiments, the process may be a dual core processor, quad core processors, other chip-level multiprocessor and the like that combine two or more independent cores (sometimes called a die).

The methods and systems described herein may be deployed in part or in whole through a machine that executes computer software on a server, client, firewall, gateway, hub, router, switch, infrastructure-as-a-service, platform-as-a-service, or other such computer and/or networking hardware or system. The software may be associated with a server that may include a file server, print server, domain server, internet server, intranet server, cloud server, infrastructure-as-a-service server, platform-as-a-service server, web server, and other variants such as secondary server, host server, distributed server, failover server, backup server, server farm, and the like. The server may include one or more of memories, processors, computer readable media, storage media, ports (physical and virtual), communication devices, and interfaces capable of accessing other servers, clients, machines, and devices through a wired or a wireless medium, and the like. The methods, programs, or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers, social networks, and the like. Additionally, this coupling and/or connection may facilitate remote execution of programs across the network. The networking of some or all of these devices may facilitate parallel processing of a program or method at one or more locations without deviating from the scope of the disclosure. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs, or codes as described herein and elsewhere may be executed by the client. In addition, other devices required for the execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of programs across the network. The networking of some or all of these devices may facilitate parallel processing of a program or method at one or more locations without deviating from the scope of the disclosure. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements. The methods and systems described herein may be adapted for use with any kind of private, community, or hybrid cloud computing network or cloud computing environment, including those which involve features of software as a service (SaaS), platform as a service (PaaS), and/or infrastructure as a service (IaaS).

The methods, program codes, and instructions described herein and elsewhere may be implemented on a cellular network with multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, 4G, 5G, LTE, EVDO, mesh, or other network types.

The methods, program codes, and instructions described herein and elsewhere may be implemented on or through mobile devices. The mobile devices may include navigation devices, cell phones, mobile phones, mobile personal digital assistants, laptops, palmtops, netbooks, pagers, electronic book readers, music players and the like. These devices may include, apart from other components, a storage medium such as flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer-to-peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g., USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, network-attached storage, network storage, NVME-accessible storage, PCIE connected storage, distributed storage, and the like.

The methods and systems described herein may transform physical and/or intangible items from one state to another. The methods and systems described herein may also transform data representing physical and/or intangible items from one state to another.

The elements described and depicted herein, including in flow charts and block diagrams throughout the figures, imply logical boundaries between the elements. However, according to software or hardware engineering practices, the depicted elements and the functions thereof may be implemented on machines through computer executable code using a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices, artificial intelligence, computing devices, networking equipment, servers, routers and the like. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps associated therewith, may be realized in hardware, software or any combination of hardware and software suitable for a particular application. The hardware may include a general-purpose computer and/or dedicated computing device or specific computing device or particular aspect or component of a specific computing device. The processes may be realized in one or more microprocessors, microcontrollers, embedded microcontrollers, programmable digital signal processors or other programmable devices, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine-readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions. Computer software may employ virtualization, virtual machines, containers, dock facilities, portainers, and other capabilities.

Thus, in one aspect, methods described above and combinations thereof may be embodied in computer executable code that, when executing on one or more computing devices, performs the steps thereof. In another aspect, the methods may be embodied in systems that perform the steps thereof and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the disclosure has been disclosed in connection with the preferred embodiments shown and described in detail, various modifications and improvements thereon will become readily apparent to those skilled in the art. Accordingly, the spirit and scope of the present disclosure is not to be limited by the foregoing examples, but is to be understood in the broadest sense allowable by law.

The use of the terms "a" and "an" and "the" and similar referents in the context of describing the disclosure (especially in the context of the following claims) is to be construed to cover both the singular and the plural, unless otherwise indicated herein or clearly contradicted by context. The terms "comprising," "with," "including," and "containing" are to be construed as open-ended terms (i.e., meaning "including, but not limited to,") unless otherwise noted. Recitations of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. The term "set" may include a set with a single member. No language in the specification should be construed as indicating any non-claimed element as essential to the practice of the disclosure.

While the foregoing written description enables one skilled to make and use what is considered presently to be the best mode thereof, those skilled in the art will understand and appreciate the existence of variations, combinations, and equivalents of the specific embodiment, method, and examples herein. The disclosure should therefore not be limited by the above described embodiment, method, and examples, but by all embodiments and methods within the scope and spirit of the disclosure.

All documents referenced herein are hereby incorporated by reference as if fully set forth herein.

What is claimed is:

1. A method for determining occupancy in a space, the method comprising:
    transmitting radio signals over a channel in the space;
    receiving the transmitted radio signals that have traveled through the space; and
    implementing with at least one processor an occupancy-centric algorithm that determines occupancy in the space based on the radio signals, that determines channel state information based on the radio signals transmitted over the channel, that determines occupancy in the space based on the channel state information, that determines a value chain recommendation based on the occupancy in the space of a value chain network, and that outputs an occupancy signal based on the determined occupancy and the value chain recommendation,
    wherein the occupancy-centric algorithm is a machine learning algorithm that analyzes the channel state information to determine the occupancy in the space, the machine learning algorithm including weights assigned to features of the channel state information, each of the weights representing how indicative of human presence its corresponding feature is, and
    wherein the occupancy-centric algorithm is adapted based on known occupancy in the space to adjust the assigned weights of the machine learning algorithm, the known occupancy is based on a signal received from a sensor that is associated with the space, and the signal indicates the known occupancy in the space as detected by the sensor.

2. The method of claim 1, wherein the value chain recommendation relates to a health of one or more workers.

3. The method of claim 1, wherein the value chain recommendation relates to allocation or reallocation of worker resources based on the occupancy in the space.

4. The method of claim 1, wherein the value chain recommendation is based on productivity of workers in the space.

5. The method of claim 1, wherein the value chain recommendation is associated with at least one of an activation or deactivation of at least one of a heating system, a ventilating system, a cooling system, a security system, a lighting system, a kitchen system, a speaker system, a power system, and an entertainment system for the space.

6. The method of claim 1, wherein the value chain recommendation is determined based on a machine learning system that trains machine-learned models that output logistics design recommendations based on training data sets that each respectively defines one or more features of a respective logistic system and an outcome relating to the respective logistics system.

7. The method of claim 1, wherein the value chain recommendation is determined based on an artificial intelligence system that receives a request for a logistics system design recommendation and determines the logistics system design recommendation based on one or more machine-learned models and the request.

8. The method of claim 1, wherein the value chain recommendation is determined by a digital twin system that generates an environment digital twin of a logistics environment that incorporates a logistics system design recommendation, and one or more physical asset digital twins of physical assets, wherein the digital twin system executes a simulation based on the logistics environment digital twin, the one or more physical asset digital twins.

9. The method of claim 1, wherein the value chain recommendation is based on logistics factors that include one or more of: a type of product corresponding to a proposed logistics solution, one or more features of the type of product, a location of a manufacturing site, a location of a distribution facility, a location of a warehouse, a location of a customer base, proposed expansion areas of an organization, and supply chain features.

10. The method of claim 1, wherein the value chain recommendation is based on logistics value chain network entities that are selected from the group consisting of products, suppliers, producers, manufacturers, retailers, businesses, owners, operators, operating facilities, customers, consumers, workers, mobile devices, wearable devices, distributors, resellers, supply chain infrastructure facilities, supply chain processes, logistics processes, reverse logistics processes, demand prediction processes, demand management processes, demand aggregation processes, machines, ships, barges, warehouses, maritime ports, airports, airways, waterways, roadways, railways, bridges, tunnels, online retailers, ecommerce sites, demand factors, supply factors, delivery systems, floating assets, points of origin, points of destination, points of storage, points of use, networks, information technology systems, software platforms, distribution centers, fulfillment centers, containers, container handling facilities, customs, export control, border control, drones, robots, autonomous vehicles, hauling facilities, drones/robots/AVs, waterways, and port infrastructure facilities.

11. The method of claim 1, wherein the value chain recommendation is based on supply factors that are selected from the group consisting of Component availability, material availability, component location, material location, component pricing, material pricing, taxation, tariff, impost, duty, import regulation, export regulation, border control, trade regulation, customs, navigation, traffic, congestion, vehicle capacity, ship capacity, container capacity, package capacity, vehicle availability, ship availability, container availability, package availability, vehicle location, ship location, container location, port location, port availability, port capacity, storage availability, storage capacity, warehouse availability, warehouse capacity, fulfillment center location, fulfillment center availability, fulfillment center capacity, asset owner identity, system compatibility, worker availability, worker competency, worker location, goods pricing, fuel pricing, energy pricing, route availability, route distance, route cost, and route safety factors.

12. The method of claim 1, wherein the value chain recommendation is determined based on a machine learning/artificial intelligence system determining a problem state based on a detected stress level of humans along a supply chain.

13. The method of claim 1, wherein the value chain recommendation is determined based on disruptions in the space of the value chain network.

14. The method of claim 1, wherein the value chain recommendation includes operating recommendations needed to compensate for changes in operating parameters.

15. The method of claim 1, wherein the value chain recommendation is determined from physical activities data and worker data in order to improve value chain workflows.

16. The method of claim 1, wherein the value chain recommendation includes suggestions for removing or limiting worker redundancies for a workflow.

17. The method of claim 1, wherein the machine learning algorithm analyzes the channel state information across one or more of spatial, temporal, or frequency domains.

18. The method of claim 1, wherein the known occupancy in the space that is utilized to adapt the occupancy-centric algorithm is further based on information manually input by a user or occupant of the space.

19. The method of claim 1, wherein the sensor includes at least one of,
a carbon dioxide ($CO_2$) sensor,
a passive infrared (PIR) sensor,
a motion sensor,
an ultrasonic sensor,
a sound sensor,
an image sensor,
a video sensor, or
a sensor of a smart home device.

20. A method for determining occupancy in a space, the method comprising:
transmitting radio signals over a channel in the space;
receiving the transmitted radio signals that have traveled through the space;
determining occupancy in the space based on the radio signals;
determining channel state information based on the radio signals transmitted over the channel;
analyzing the channel state information by a machine learning algorithm to determine the occupancy in the space based on the channel state information, wherein the machine learning algorithm includes weights assigned to features of the channel state information, each of the weights representing how indicative of human presence its corresponding feature is;
determining a value chain recommendation based on the occupancy in the space of a value chain network;
outputting an occupancy signal based on the determined occupancy and the value chain recommendation;
receiving a signal from a sensor that is associated with the space, wherein the signal indicates a known occupancy in the space as detected by the sensor; and
adjusting the assigned weights of the machine learning algorithm based on the signal received from the sensor.

* * * * *